(12) United States Patent
Srivastava et al.

(10) Patent No.: US 7,702,430 B2
(45) Date of Patent: Apr. 20, 2010

(54) METHOD FOR DESIGNING A POTENTIAL INHIBITOR OF GLUTATHIONE-ALDEHYDE CONJUGATE BINDING TO ALDOSE REDUCTASE

(75) Inventors: Satish K. Srivastava, Galveston, TX (US); Aurni Bhatnagar, Prospect, KY (US); Kota V. Ramana, Galveston, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 0 days.

(21) Appl. No.: 11/282,801

(22) Filed: Nov. 18, 2005

(65) Prior Publication Data

US 2006/0110814 A1 May 25, 2006

Related U.S. Application Data

(60) Provisional application No. 60/629,448, filed on Nov. 19, 2004.

(51) Int. Cl.
*G05D 1/00* (2006.01)
*A61K 38/44* (2006.01)

(52) U.S. Cl. ........................................ 701/11; 424/94.4

(58) Field of Classification Search ....................... None
See application file for complete search history.

(56) References Cited

OTHER PUBLICATIONS

Giege et al. (1994) Acta Cryst., D50, 339-350.*
Branden et al (1999) Introduction to Protein Structure, Second Edition, Garland Publishing Inc., New York, pp. 374-375 and 382.*
Drenth (1995) Principles of X-ray Crystallography, Springer, New York, p. 1.*
Kierzek et al. (2001) Biophys Chem, 91:1-20.*
Wiencek (1999) Ann Rev Biomed Eng., 1:505-534.*
Iwata et al. 2001, Drug Des Discov., vol. 17, pp. 349-359.*
Iwata et al. 2001, J. Med. Chem., vol. 44, pp. 1718-1728.*

* cited by examiner

*Primary Examiner*—David J Steadman
*Assistant Examiner*—Alexander D Kim
(74) *Attorney, Agent, or Firm*—Benjamin Aaron Adler

(57) ABSTRACT

Provided herein is a crystallized ternary structure of human aldose reductase (AR) bound to NADPH and γ-glutamyl-S-(1,2-dicarboxyethyl)cysteinylglycine (DCEG). Also provided are specific inhibitors of glutathione-aldehyde binding to aldose reductase which are designed via at least computer modeling of the ternary AR:NADPH:DCEG structure and methods of designing and of screening the inhibitors for inhibition of glutathione-aldehyde binding to aldose reductase.

5 Claims, 18 Drawing Sheets

METHOD FOR DESIGNING A POTENTIAL INHIBITOR OF GLUTATHIONE-ALDEHYDE CONJUGATE BINDING TO ALDOSE REDUCTASE

CROSS-REFERENCE TO RELATED APPLICATION

This non-provisional application claims benefit of provisional U.S. Ser. No. 60/629,448 filed Nov. 19, 2004, now abandoned.

FEDERAL FUNDING LEGEND

This invention was produced in part using finds obtained through Grants DK36118 and EY01677 from the National Institutes of Health. Consequently, the federal government has certain rights in this invention.

BACKGROUND OF THE INVENTION

1. Field of the Invention

The present invention relates generally to the fields of enzymology, protein structure and drug screening. More specifically, the present invention relates to the use of a crystalline structure of an aldose reductase complexed with NADPH and glutathione conjugate as a screening tool for inhibitors of aldose reductase.

2. Description of the Related Art

Aldose reductase (AR) is a monomeric (a/b$_8$-barrel (TIM barrel) protein belonging to the aldo-keto reductase (AKR) superfamily (1-3). Aldose reductase is a broad-specificity oxidoreductase catalyzing the reduction of a structurally-diverse range of aldehydes, including medium to long chain aldehydes, glucose and other aldo-sugars, aldehyde metabolites of neurotransmitters, isocorticosteroid hormones, and a variety of xenobiotic aldehydes to their corresponding alcohols (4). Reduction of glucose to sorbitol by aldose reductase constitutes the first and rate-limiting step of the polyol pathway that converts glucose to fructose via sorbitol dehydrogenase. Although this pathway usually represents a minor route of glucose metabolism, its activation during diabetes has been linked to the development of several clinically significant secondary complications such as nephropathy, neuropathy, retinopathy and cardiovascular related complications (4, 5). Several drugs that inhibit aldose reductase have been shown to prevent hyperglycemia-induced changes in nerve, kidney, and lens of experimental animals, although clinical trials with Type I and Type II diabetics have not been uniformly positive (4-6).

In addition to glucose, it has been shown that aldose reductase catalyzes the reduction, of multiple biologically-active aldehydes generated by the peroxidation of membrane lipids and lipoproteins (7-9) or during glucose (10) and amine (11) metabolism. The aldehyde-detoxifying role of aldose reductase is supported by the observation that inhibition of the enzyme increases the accumulation of lipid peroxidation products (12, 13) that cause cytotoxicity (14, 15). The most abundant and toxic lipid peroxidation product is 4-hydroxy-trans-2-nonenal (16) which is efficiently reduced by aldose reductase in vitro and in vivo.

A primary role of aldose reductase in aldehyde detoxification is consistent with its structure. The active site of the enzyme is highly hydrophobic and contains few polar residues typically required for binding sugars with high specificity and affinity (2, 3). These features are, however, compatible with binding to hydrophobic lipid-derived aldehydes. Additionally, the substrate-specificity of aldose reductase is unusually broad, in part because the enzyme derives most of the energy required to achieve a substrate transition state from cofactor-binding (17). The active site environment exerts low stabilization on the transition state (18). Furthermore, it has been demonstrated recently that aldose reductase-catalyzed products mediate cytokine, chemokine, growth factor, and hyperglycemia-induced signaling that activates NF-kB and AP1, and regulates vascular epithelial cell (VEC) and human lens epithelial cell (HLEC) apoptosis, and vascular smooth muscle cell (VSMC) proliferation (FIG. 1) (15, 21, 22).

The range of aldehydes recognized by the aldose reductase active site is increased further by the ability of the enzyme to bind glutathione-aldehyde conjugates (19, 20), such as glutathionyl HNE. Given the high concentration of reduced glutathione in most cells and the highly electrophilic nature of several aldose reductase substrates, it is possible that reduction of aldehyde-glutathione conjugates, in addition to free aldehydes, may be a primary in vivo function of aldose reductase and that glucose may be an incidental substrate of the enzyme. Previous kinetic studies showed that glutathiolation increases the catalytic efficiency with which unsaturated aldehydes are reduced by aldose reductase (19), suggesting that the active site of aldose reductase contains a specific glutathione-binding domain (20). Nevertheless, the precise nature of glutathione binding to aldose reductase remained unclear.

There is a need in the art for three-dimensional structures of aldose reductase-glutathione-moiety binding complexes to understand the nature of glutathione-moiety binding at the active site. Also there is a need for methods incorporating computer modeling of three-dimensional structures to identify, design and test molecules with improved binding affinity. A further need for molecules that would be useful as therapeutics and/or modulators of aldose reductase-mediated physiological events is also present in the art.

The prior art is deficient in structure based aldose reductase inhibitors that preferentially occlude one binding site in the inhibitor. Specifically, the prior art is deficient in the lack of aldose reductase:NADPH:glutathione-like ligand based inhibitors that inhibit binding and reduction of glutathione-lipid aldehyde conjugates without inhibiting the detoxification of free aldehydes. The present invention fulfills this long-standing need and desire in the art.

SUMMARY OF THE INVENTION

The present invention is directed to a crystalline structure of a ternary AR:NADPH:glutathione-like ligand complex. The crystalline structure diffracts x-rays for determining atomic co-ordinates of said complex with a resolution of about 3 Å to about 1.94 Å. The glutathione-like ligand interacts with both a glutathione binding domain and a carbonyl binding site within an active pocket formed by an AR:NADPH complex within the ternary structure. The present invention also is directed to a related crystalline structure comprising a ternary AR:NADPH:DCEG complex diffracts x-rays for determining atomic co-ordinates of the complex with a resolution of about 1.94 Å.

The present invention also is directed to a method of designing a potential inhibitor of glutathione-aldehyde conjugate binding to aldose reductase. The method comprises identifying a glutathione-like ligand that interacts with the glutathione binding domain, but does not block the carbonyl binding site, in the active pocket of an aldose reductase which has the three-dimensional conformation determined by DCEG binding to AR:NADPH. The identification of the potential inhibitor is based at least in part on a computer model of the crystalline AR:NADPH:DCEG ternary structure described herein.

The present invention is directed to a related method of screening for inhibitors of glutathione-aldehyde conjugate reduction by aldose reductase. The method comprises using the crystalline ternary structure described herein to design a potential inhibitor that binds to the glutathione binding domain in aldose reductase, but does not interfere with the carbonyl binding site. The design is based in part on computer modeling of the crystalline AR:NADPH:DCEG. The aldose reductase is complexed with the potential inhibitor and the aldose reductase:inhibitor complex is contacted with a lipid aldehyde and with the lipid aldehyde conjugated to glutathione. Detection of a reduced lipid aldehyde product, but not a reduced glutathione-lipid aldehyde product, screens for the inhibitor.

The present invention is directed further to the specific inhibitors of glutathione-aldehyde conjugate reduction designed and screened for by the methods described herein.

The present invention is directed further yet to a method of preventing a pathophysiological state or treating symptoms thereof resulting from aldose-reductase mediated signaling of a cytotoxic pathway in an individual. The method comprises administering a pharmacologically effective amount of the inhibitors of glutathione-aldehyde conjugate reduction described herein to the individual and inhibiting the reduction of a glutathione-aldehyde substrate via aldose reductase to prevent cytotoxic signaling in the individual. The cytotoxic signals could be generated by cytokines, chemokines, reactive oxygen species, endotoxins, growth factors, hyperglicemia and biologically active agents, e.g., bioterrorism agents.

Other and further aspects, features, and advantages of the present invention will be apparent from the following description of the embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate embodiments of the invention and therefore are not to be considered limiting in their scope.

FIG. 2A is the DCEG structure showing hydrogen bond interactions with aldose reductase and solvent as hashed lines. The dashed semi-circles denote hydrophobic interactions with the protein. FIG. 2B is a ribbon drawing of AR:NADPH (purple) with DCEG bound (yellow ball-n-stick). The β-strands in the $(\tilde{\alpha}\beta)_8$ barrel are colored cyan. The mobile active loops A, B, and C are colored red, green, and blue, respectively.

FIG. 3A shows a top view of the human aldose reductase molecular surface (purple) with the active site occupied by DCEG (yellow). For clarity, solvent atoms have been omitted. FIG. 3B shows a close-up view of DCEG (yellow ball-stick) and the two waters bound in the aldose reductase active site. The active site residues: Tyr-48, His-110, Trp-110, and NADPH, sit at the base of the deep cleft where the DCEG dicarboxyethyl moiety is bound. Coloring is the same as for FIG. 2B.

FIG. 5A shows the PGE2 release in the medium which was determined by using monoclonal enzyme immuno assay kit and the pooled cell extracts from three independent experimental sets were subjected to SDS-PAGE and Western blots were developed using antibodies anti-Cox-2 (FIG. 5B).

FIG. 10 illustrates the effect of AR inhibition on LPS-induced cardiac dysfunction.

DETAILED DESCRIPTION OF THE INVENTION

Figure 1:
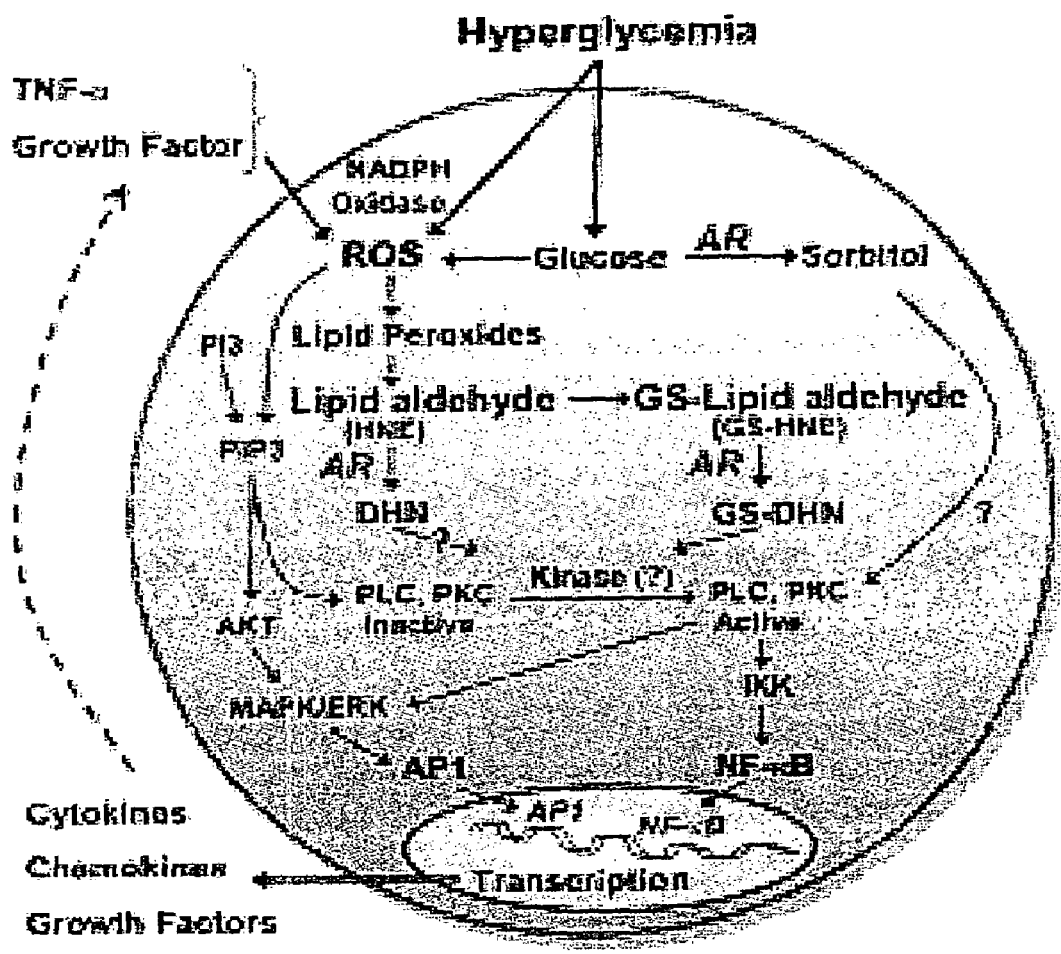
FIG. 1 depicts the mediation of cytotoxic signals by aldose reductase. Cytokines, growth factors and hyperglycemia generate reactive oxygen species (ROS) and cause peroxidation of lipids resulting in the generation of toxic lipid aldehydes such as 4-hydroxynonenal (HNE). Aldose reductase efficiently reduces hydroxynonenal and its conjugate with GSH to DHN and GS-DHN, respectively. The reduced products of aldehydes may be involved in the cytotoxic signaling leading to cell death or growth via activation of PLC/PKC/NF-kB and AP1 pathway.

In one embodiment of the present invention there is provided a crystalline structure of a ternary AR:NADPH:glutathione-like ligand complex, wherein the crystalline structure diffracts x-rays for determining atomic co-ordinates of the complex with a resolution of about 3 Å to about 1.94 Å and wherein the glutathione-like ligand interacts with both a glutathione binding domain and a carbonyl binding site within an active pocket formed by an AR:NADPH complex within the ternary structure.

In one aspect of this embodiment, the ternary structure has a space group of $P2_1$ and a unit cell with dimensions of a=47.21 Å, b=66.72 Å and c=49.30 Å. In this aspect the crystalline structure has the protein data base accession code of 1Q9N. In a related aspect the active pocket comprises three flexible loops A, B, and C where the glutathione-like ligand interacts with at least the C loop. An example of the glutathione-like ligand is γ-glutamyl-S-(1,2-dicarboxyethyl) cysteinylglycine.

In a related embodiment there is provided a crystalline structure of a ternary AR:NADPH:DCEG complex wherein the crystalline structure diffracts x-rays for determining atomic co-ordinates of the complex with a resolution of about 1.94 Å. The crystalline structure has the protein data base accession code of 1Q9N.

In another embodiment of the present invention there is provided a method of designing a potential inhibitor of glutathione-aldehyde conjugate binding to aldose reductase, comprising identifying a glutathione-like ligand that interacts with the glutathione binding domain, but does not block the carbonyl binding site, in the active pocket of an aldose reductase having a three-dimensional conformation determined by DCEG binding to AR:NADPH, where the identification is based at least in part on a computer model of the crystalline AR:NADPH:DCEG ternary structure described supra.

Further to this embodiment the method comprises screening the potential inhibitors for inhibition of glutathione-aldehyde conjugate reduction by aldose reductase. Screening may comprise contacting aldose reductase with the potential inhibitor, contacting the AR:inhibitor complex with a lipid aldehyde and with the lipid aldehyde conjugated to glutathione and detecting only a reduced lipid aldehyde product.

In this embodiment, the glutathione-binding domain comprises residues Trp-20, Trp-79, Trp-111, Trp-219, Phe-122, Val-47, Cys-298, Ala-299, Leu-300, Ser-302 and Leu-301. In an aspect of this embodiment the residues Ser-302, Ala-299, Leu-300, and Leu-301 comprise a C loop of the active pocket. Particularly in this aspect Ser-302, Ala-299, Leu-300, and Leu-301 interact with the glutathione-like ligand via a network of water molecules within the C loop. Also in this embodiment the carbonyl binding site comprises residues Tyr-48, His-110, and Trp-111 and NADPH. A representative example of a glutathione-like ligand has a γ-glutamylcysteinylglycine backbone with an S-cysteinyl -substituted moiety.

In a related embodiment there is provided a method of screening for inhibitors of glutathione-aldehyde conjugate reduction by aldose reductase, comprising using the crystalline structure of the ternary AR:NADPH:DCEG described supra to design a potential inhibitor that binds to the glutathione binding domain in aldose reductase, but does not interfere with the carbonyl binding site, where the design is based at least in part on computer modeling; contacting aldose reductase with the potential inhibitor; contacting the AR:inhibitor complex with a lipid aldehyde and with the lipid aldehyde conjugated to glutathione; and detecting a reduced lipid aldehyde product, but not a reduced glutathione-lipid aldehyde product, thereby screening for the inhibitor.

In yet another embodiment there is provided an inhibitor of glutathione-aldehyde conjugate reduction by aldose reductase designed by the methods described supra. In a related embodiment there is provided a method of preventing a pathophysiological state or treating symptoms thereof resulting from aldose-reductase mediated signaling of a cytotoxic pathway in an individual, comprising administering a pharmacologically effective amount of the inhibitor described supra to the individual; and inhibiting the reduction of a glutathione-aldehyde substrate via aldose reductase, thereby preventing the cytotoxic signaling in the individual. An example of a cytotoxic pathway is PLC/PKC/NF-κB.

In a related embodiment there is provided a method to reduce the deleterious NF-kB dependent inflammatory processes following a bacterial infection comprising administering a pharmacologically effective amount of the inhibitor described supra to the individual.

In a related embodiment there is provided a novel therapeutic approach in preventing colon cancer by administering a pharmacologically effective dose of the inhibitor described supra. Inhibition of aldose reductase significantly reduces HNE or GS-HNE induced up regulation of cyclo oxygenase (Cox-2) and type 2 prostaglandin (PGE2). Inhibition of PGE2 and Cox-2 is known to reduce the risk of colon cancer progression.

The following abbreviations are used herein: AR: human aldose reductase, ARL2, E.C. 1.1.1.21; sAR: *Sus scrofa* (Pig) aldose reductase, AR, E.C. 1.1.1.21; NADPH: dihydro-nicotinamide-adenine-dinucleotide phosphate; NADP: nicotinamide-adenine -dinucleotide phosphate; DCEG: S-(1,2-dicarboxyethyl)glutathione, γ-glutamyl-S-(1,2-dicarboxyethyl) cysteinylglycine; ROS: reactive oxygen species; CNS: Crystallography and NMR Software; GS: glutathione; γ-glutamylcysteinylglycine.

Provided herein is a crystallized ternary complex of human aldose reductase bound to NADPH and γ-glutamyl-S-(1,2-dicarboxyethyl)cysteineinylglycine, a competitive inhibitor of AR-catalyzed reaction of glutathionyl-propanal (19). The ternary structure confirms the presence of two active sites within AR:NADPH. The crystal structure was determined to 1.9 Å and revealed novel interactions between the glutathione backbone and active site residues.

The ternary structure demonstrates that DCEG binding induces a significant conformational reorganization of the active site. The carboxylate moiety of DCEG binds in the aldose reductase active site, while the GS C-terminus binds in the aldose reductase loop C. The binding of glutathione to aldose reductase significantly reorients loops A and B of the protein thereby providing an induced-fit mechanism that enables the active site to bind substrates of different sizes. This induced-fit rearrangement and the multiplicity of specific interactions at the aldose reductase active site with glutathione are indicative of a highly selective glutathione-binding domain.

Thus, the ternary structure is used in methods of developing therapeutic inhibitors that selectively prevent binding of glutathione-conjugated substrates. These structure-based inhibitors are designed using rational drug design in conjunction with computer modeling of the coordinates of the ternary crystalline structure. The coordinates indicate that structure based inhibitors could be synthesized which will inhibit the glutathione-aldehyde binding site without affecting the detoxification role of aldose reductase since it will not inhibit the carbonyl binding site. For example, the specific inhibitors would not interfere the detoxification of free aldehydes, such as 4-hydroxy trans-2 nonenal which is formed during lipid peroxidation.

Also provided are the designed structure-based inhibitors and methods of screening therefor. The aldose reductase inhibitors may function through one of two mechanisms. Either remodeling of the aldose reductase loop-C backbone or steric hindrance of the GS-specific binding site in this loop may prevent the binding of GS-conjugates and their entry into the aldose reductase active site. A designed inhibitor may comprise a γ-glutamylcysteinylglycine backbone with an S-cysteinyl-substituted moiety that does not interfere with aldehyde binding to aldose reductase at the carbonyl active site.

These designed inhibitors may be tested for selective inhibition of glutathione-aldehyde binding in a screening assay. A selective inhibitor will form a complex with aldose reductase in the presence of NADPH by binding or otherwise interacting within the glutathione-binding domain in aldose reductase. Such a specific inhibitor will exclude glutathione-aldehyde binding and prevent subsequent reduction of the glutathione-aldehyde, but will not interfere with binding and reduction of the unconjugated lipid aldehyde at the carbonyl active site. Such screening assays are standard and well within the ordinary skill of an artisan to implement without undue experimentation or burden.

It is contemplated that the aldose reductase inhibitors provided herein may be used as a therapeutic to treat or modulate or otherwise alter a pathophysiological state or event or symptoms thereof mediated by reduction products of aldose reductase as part of the pathology. For example, and without being limiting, a specific inhibitor could prevent glutathione binding without affecting the carbonyl reduction necessary to detoxify lipid aldehydes. Such inhibition could regulate TNF-α, growth factor, lipopolysaccharide and hyperglycemia-induced cytotoxicity mediated by reactive oxygen species in for example, the PLC/PKC/NF-κB pathway. It is further contemplated that such an inhibitor may limit access of other bulky molecules, such as glucose, to the AR active site thereby reducing other adverse effects of hyperglycemia as mediated by AR's role in the osmotic stress pathway.

It is standard in the art to formulate a therapeutic compound with a pharmaceutically acceptable carrier as a pharmaceutical composition. It is also standard in the art to determine dose, dosage and routes of administration of the therapeutic or pharmaceutical compounds. Such determination is routinely made by one of skill in the art based on the individual and the particular pathophysiological state or symptoms exhibited by the patient and the patients history.

It is further contemplated that other AKR proteins have similar sites that are capable of high affinity interactions with glutathione or glutathione conjugates. The same or similar techniques used to elucidate the AR:NADPH:DCEG ternary structure may be used to determine the coordinates of other similar AKR:ligand three-dimensional structures. Such crystal structures may be used in the design of relevant therapeutic inhibitors.

The following examples are given for the purpose of illustrating various embodiments of the invention and are not meant to limit the present invention in any fashion.

EXAMPLE 1

Overexpression and Purification of Recombinant Human AR

Recombinant human AR (SEQ ID NO: 1) was overexpressed and purified as described earlier (23). In brief, the cell extract was subjected to chromatofocusing on PBE94 (Pharmacia LKB Biotechnology Inc.) followed by hydroxylapatite column chromatography and reactive blue affinity chromatography as the final step. All purification buffers contained 1 mM dithiothretiol (DTT).

EXAMPLE 2

Crystallization of the Ternary Complex

Purified AR was concentrated by ultrafiltration (Amicon YM-10 membrane) to ~10 mg/ml. Prior to crystallization, 10 mg/ml AR in phosphate buffer (10 mM phosphate pH 7.1, 0.5 mM EDTA, 10 mM DTT) was incubated with NADPH and DCEG (γ-glutamyl-S-(1,2-dicarboxyethyl)glutathione) at a AR:NADPH:DCEG molar ratio of 1:2:2 for 10 min at 4° C. The ternary complex was crystallized using the vapor diffusion method at 4° C. The protein:ligand solution was mixed with an equal volume of 22% (w/v) polyethylene glycol (PEG) 4000 in 100 mM sodium citrate (pH 5.0) and 6 ml of droplets were placed above an identical well solution.

EXAMPLE 3

Data Collection

X-ray data were collected using a MacScience DIP 2030H area detector and a M06XHF rotating anode X-ray generator operating at 50 KV and 90 Ma and equipped with Göbel collimating optics (Bruker AXS). The first crystal, 0.1×0.1× 0.1 mm$^3$, was flash-cooled, without the addition of cryoprotectants to the drop, using nitrogen boil-off (Cryo Industries). Weak ice rings were observed in the diffraction pattern. The protein crystallized in the $P2_1$ monoclinic space group with cell dimensions a=47.21 Å, b=66.72 Å, c=49.30 Å, a=g=90.00°, b=92.24°. This crystal form was not observed previously for any AR crystal structures. Based upon the Matthews coefficient (24), there was predicted to be one AR molecule per au. The data were processed to 2.6 Å resolution using the programs HKL (25).

A second crystal was soaked in mother liquor containing 20% glycerol (v/v) and 25 mM of DCEG and flash cooled. Diffraction data collected from crystal 2 were processed with HKL to 1.94 Å resolution and was used for high-resolution refinements of the model. Space group and unit cell dimensions were similar to crystal 1. Data collection and processing statistics, including atomic coordinates and structure factors for crystal 2, i.e., 1Q9N, are shown in Table 1.

TABLE 1

Summary of crystallographic statistics

| | |
|---|---|
| AR Sequence | SEQ ID NO: 1 |
| Space group | $P2_1$ |
| Cell | |
| a (Å) | 47.21 |
| b (Å) | 66.72 |
| c (Å) | 49.30 |
| a(°) | 90.00 |
| b (°) | 92.24 |
| g (°) | 90.00 |
| Data Collection | |
| Resolution range, Å | 30–1.94 |
| $R_{merge}$, * % | 9.0 (30.7) |
| Unique observations | 22,256 |
| Average I/s(I) * | 13.8 (4.4) |
| Redundancy * | 5.8 (3.2) |
| Completeness * % | 97.7 (87.8) |
| Refinement Statistics | |
| R-factor (%) * | 21.1 (26.4) |
| $R_{free}$, * % | 26.0 (34.9) |
| r.m.s. deviations | |
| Bonds (Å) | 0.006 |
| Angles (°) | 1.3 |
| Model Statistics | |
| No. residues in most favored region | 249 |
| Additional allowed | 25 |
| Generously allowed | 3 |
| Disallowed | 0 |
| No. Protein Atoms | 2517 |
| No. Ligand atoms | 76 |
| No. Waters | 165 |
| Average B factor (Å$^2$) | 20.4 |
| Protein (Å$^2$) | 19.4 |
| Waters (Å$^2$) | 25.1 |

* Values for the highest-resolution shells are given in parentheses.

EXAMPLE 4

Structure Determination and Refinement

The $P2_1$ crystal form structure was solved by molecular replacement using the program EPMR (26) with the 1ADS (3) structure as a search model. Initial model building in CNS (27) used data collected to 2.6 Å resolution from crystal 1. Since this data set contained scattering noise from ice crystals, the initial refinement contained resolutions shells with unusually high R-factors. An alternate processing of this data, which removed all reflections in the narrow resolution range affected by the ice, also was used for model building.

The PMB suite of programs (28) was used to generate a test set using 5% of the reflections chosen in thin shells equally spaced in 1/d. The PMB suite was used as an interface to the structure refinement program CNS to simplify and partially automate the structure refinement process. The variable sigma model of B-factor restraints (29) was implemented in CNS and the parameters optimized to minimize the free R. This led to a significant reduction in the free R value. The result was a model that had the least bias without over-fitting free parameters (30, 31).

An initial rigid body refinement was followed by repetitive rounds of isotropic variable sigma B-factor and positional refinement, until the free R factor (32) no longer decreased (The PMB software suite is available from the author M.A.W. (http://www.xray.utmb.edu/PMB)). The model was rebuilt in iterative rounds of model building (Xtalview (33)) and refinement. Structure factors were corrected for anisotropic scattering and absorption using a local scaling algorithm (28, 34, 35). The DCEG (FIG. 2A) inhibitor was modeled using Insight II (Accelrys, San Diego, Calif.) and energy minimized using the PRODRG web server (36), which also generated the stereochemical restraints used in the structure refinement.

The second $P2_1$ crystal structure was solved using the partially refined 2.6 Å model. The initial rigid body refinement was followed by repetitive rounds of individual atomic isotropic variable sigma B-factor and positional refinement, until the free R factor no longer decreased. Model building included the examination of waters selected by CNS. Waters with excessive B-factors (>60 Å$^2$) or poor density correlation were deleted.

Model quality was assessed after each refinement step with XtalView or PROCHECK (37). Refinement of the final model proceeded in parallel with alternate conformations of the DCEG ligand. The model with the lowest free R was chosen as the final model. The DCEG ligand of this model produced the best fit to the electron density from the two separate refinements. Multiple conformation refinement of DCEG in REFMAC (38, 39), including TLS anisotropic B-factors, with a single AR model and the two DCEG models confirmed that the chosen conformation had the highest correlation with the observations. All molecular figures were generated using PYMOL (40).

EXAMPLE 5

Overall Structure

Figure 2A:
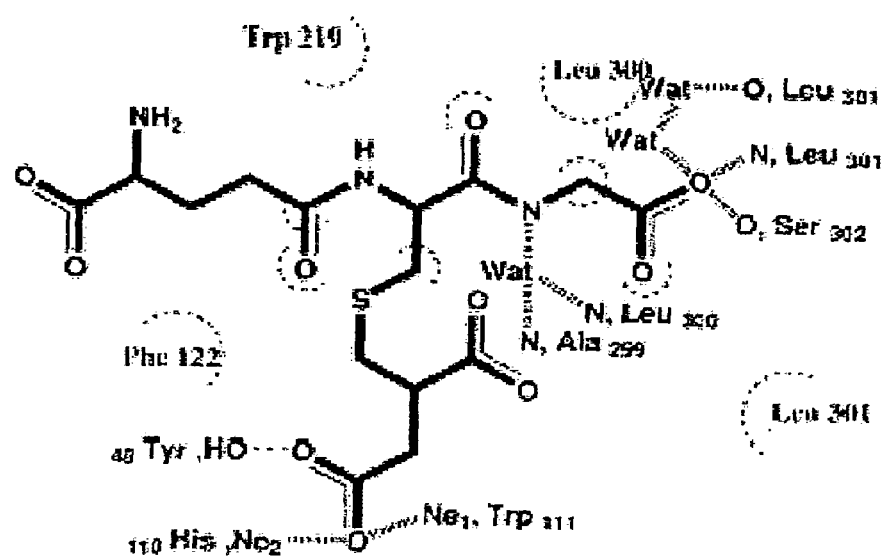
FIGS. 2A-2B depict the structure of DCEG and human aldose reductase.
Figure 2B:
Figure 3A:
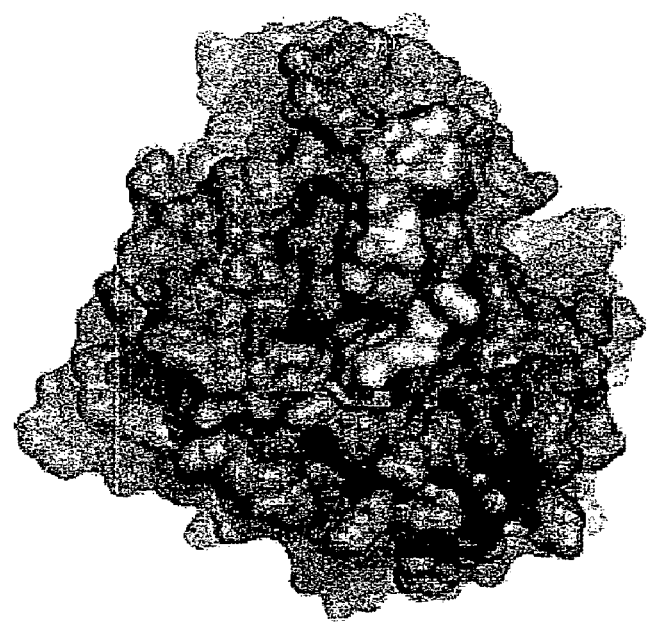
FIGS. 3A-3B depict the human aldose reductase active site with DCEG bound.

The AR:NADPH:DCEG ternary complex structure was refined to 1.94 Å resolution with a final R-factor of 21.6%. This structure showed well-defined electron density for the DCEG substrate at the "top" of aldose reductase active site pocket (FIG. 2B). The DCEG was bound between two opposing surfaces of the active site pocket, but did not completely fill the active site cleft (FIG. 3A). The DCEG substrate made ~80 contacts, defined as inter-residue distances ≦4 Å, with residues in the active site cleft (FIG. 2A). The majority of these intermolecular contacts were hydrophobic. The NADPH binding site was located at the base of the aldose reductase hydrophobic active site pocket and the NADPH cofactor was bound to the ternary complex in an orientation identical to that observed in previously reported crystal structures (3, 41, 42).

The active site of aldose reductase sat at the base of a deep cleft or binding pocket. The sides of the active site pocket were formed by three flexible loops A, B, and C (43) which sat on top of the aldose reductase $(\alpha\beta)_8$ barrel (FIG. 2B). The active site comprises residues Tyr-48, His-110, and Trp-111.

Figure 3B:
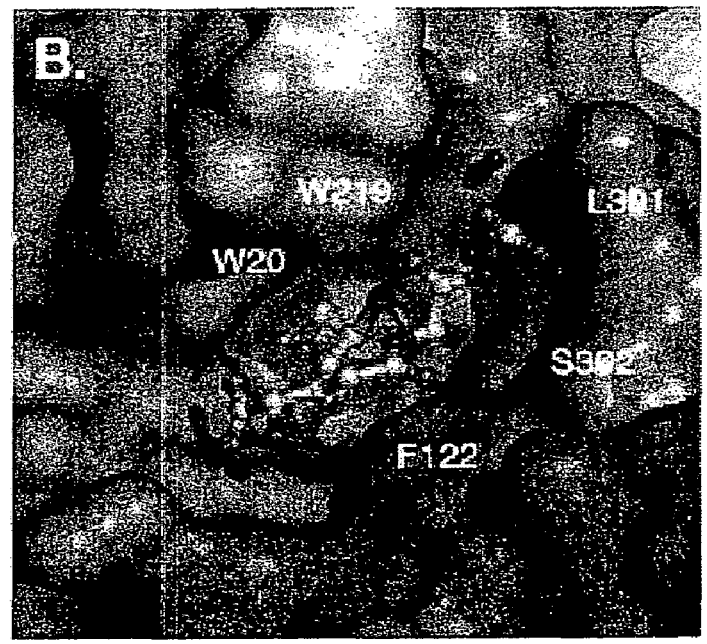

DCEG was bound in the active site almost filling the active site pocket. Trp-219 forms one side of the narrow pocket holding the inhibitor DCEG (FIG. 3B). The other residues lining this pocket included Trp-20, Trp-79, Trp-111, Phe-122, NADPH, Val-47, Cys-298, Ala-299, Leu-300, and Leu-301.

EXAMPLE 6

DCEG Interactions with AR

The C-terminal glycine moiety of DCEG was extensively hydrogen bonded to the backbone atoms of residues 300-302 in the flexible human aldose reductase C-terminal loop (loop-C). In addition, the ligand made several van der Waals contacts with aldose reductase. Several bound water molecules mediated the interaction between the DCEG glycine moiety and aldose reductase. The amides of Ala-299 and Leu-300 were bound indirectly to DCEG through a water molecule. The terminal carboxylate group of the DCEG interacted with the backbone of Leu-301 and Ser-302 and indirectly with Leu-301 through a network of waters (FIG. 2A). These residues were in human aldose reductase loop C which has been shown to be important for enzymatic activity. Mutations within this loop result in drastically lowered human aldose reductase activity (44).

The dicarboxyethyl group of DCEG was anchored in the conserved anion-binding site between the nicotinamide ring of the NADPH cofactor and aldose reductase residues Tyr-48, His-110, and Trp-111 similar to other known aldose reductase inhibitors (41,42). The terminal carboxylates of the dicarboxyethyl conjugate's longer arm, Oi2 and Oj2, were hydrogen bonded to active site residues His-110, Tyr-48, and Trp-111 (FIG. 2A, 3B). The γ-glutamate of DCEG was observed to interact with the AR enzyme only through van der Waals contacts with Phe-122 that formed one side of the hydrophobic active site pocket. The lack of hydrogen bonds or extensive contacts permitted the γ-glutamate moiety significant conformational freedom.

The higher temperature factors for these atoms reflected the relative disorder in the N-terminal end of DCEG. The hydrophobic walls of the upper portion of the aldose reductase active site pocket were formed in large part by Trp-219 and Phe-122, similar to the structures observed in other AR:inhibitor complexes (41, 42). These two aromatic residues tightly constrained the position of the cysteine moiety in DCEG. The Phe-122 and Trp-219 side chains could move slightly to accommodate differently sized inhibitors. The extensive van der Waals contacts with Trp-20 observed in the aromatic inhibitors tolrestat, zopolrestat, and sorbinil were completely absent in DCEG. The Trp-20 and Trp-79 residues, although still defining the active site pocket, did not interact with DCEG directly. They did, however, limit the conformational space available to the DCEG molecule.

The conformation of the glutathione (GS)-moiety of the AR-bound DCEG (FIG. 3B) was similar to the conformation of GS observed in the GS-binding proteins glutathione-S-transferase (45), sphingomonad GST (1fe2 (46)), human thioltransferase (47), yeast prion URE2P (48), and the chloride intercellular channel (49). The GS backbone conformation of DCEG was most distinct from the conformation of GS bound to glutatione reductase (1b4q (47), 1gra (50)). The GS conformation of AR-bound DCEG adopted the low energy Y-shape, rather than the V-form of GS observed in glutaredoxin (47), glutathione reductase (47, 50), and glutathione peroxidase (51, 52) complexes.

The GS backbone of DCEG overlapped with the GS structures with root mean square deviations (rmsd) from 0.4 to 1.4 Å. The largest rmsd between the observed structures of GS bound to several different enzymes and DCEG bound to aldose reductase occurred in the N- and C-terminal atoms. In comparison with GS bound to glutathione reductase, the cysteine of DCEG bound to aldose reductase had a y angle that was rotated by ~180 degrees. The aldose reductase-bound DCEG glutathione backbone conformation was most similar to that observed in GS complexes with hematopoietic prostaglandin d synthase (53) or yeast prion URE2P (48).

DCEG binding to aldose reductase lacks the N-terminal hydrogen bonds seen in the other GS:protein complexes. The placement of the GS backbone was largely determined by the interaction of the conjugate with the active site of the enzyme and the mobile loop-C. The van der Waals interactions with the binding cleft were nonspecific and allowed for flexibility of the GS moiety.

EXAMPLE 7

Comparison with Other AR Structures

The structure of the human aldose reductase enzyme within the ternary complex showed significant conformational differences relative to the AR:NADPH binary complex (3). The backbone atoms of Pro-123 to Val-131 in loop A and Pro-218 to Pro-225 in loop B, which flank the active site pocket, were reoriented >5 Å upon DCEG binding relative to the binary structure. The AR:NADPH:DCEG ternary complex more closely resembled the AR:NADP:zopolrestat (54) and AR:NADP:Idd384 (41) ternary complexes than the AR:NADPH binary complex. In the ternary complexes the largest relative atomic movements, with rmsd>1 Å, occurred in the region of Ser-127, Pro-222, and Leu-300.

The conformation of loop B, residues Pro-218 to Pro-225, was very similar in all of the AR structures, with just the backbone conformation of residues Pro-222 and Asp-224 flipping in the holoenzyme. Loop A of the holoenzyme structure (3) displayed a completely different conformation for this entire loop region relative to the current complex. Loop C was observed in two different conformations, which depended on the size and shape of the inhibitor bound in the solved AR structures. The conformation of loop C in AR:NADPH:DCEG had the greatest similarity to the human aldose reductase structures found in the AR:NADPH holoenzyme (3) and AR:NADPH:Idd384 ternary complex (41). Additionally, loop C in the current structure had large positional differences with the conformation observed in the zoplorestat and tolrestat ternary complexes (42). This indicated that loop C was dynamic and could move to accommodate larger molecules such as zopolrestat and tolrestat. The smaller sorbinil inhibitor did not change this loop's conformation significantly (42).

EXAMPLE 8

Comparison with Molecular Dynamics Models

Based on molecular dynamics (MD) simulations on a GS-propanal conjugate binding to human aldose reductase (19), two possible alternate conformations of the bound substrate were proposed. The observed structure of DCEG in the AR:NADPH:DCEG ternary complex was very similar to the first, lowest energy model (Model 1) of our molecular dynamics simulation, i.e., 0.8 Å overall rmsd on the GS-backbone and 0.5 Å rmsd, excluding the disordered N-terminus of the substrate. The small variations between the model and DCEG structure could be attributed to the change in the active-site atoms from carbonyl in GS-propanal to a carboxylate in DCEG, and the conformational freedom of the γ-glu N-terminus.

It has been demonstrated that DCEG is a competitive inhibitor of aldehyde reduction by aldose reductase, indicating that the conjugate bound selectively to AR:NADPH and had little or no affinity for the enzyme of the AR:NADP$^+$ binary complex. The reasons for this behavior are apparent from the current structure. The non-specific interactions of DCEG with the active site cleft and loose shape complimentarity are consistent with a very low affinity of DCEG for apo AR.

The result of NADPH binding is rearrangement of the active site residues Tyr-48, His-110 and Trp-111, plus the adjacent A, B, and C loops. Thus, NADPH binding reorients these regions to form the active site pocket. It is only after these rearrangements that AR would have any significant affinity for DCEG. Therefore, DCEG binding must be preceded by formation of the holoenzyme AR:NADPH complex.

In the AR:NADPH:DCEG ternary complex, a larger percentage, i.e., 50%, of DCEG is buried by AR side chains than has been observed in structures of other GS-binding proteins (40-45%), suggesting that the strongly aliphatic nature of DCEG, which allows multiple contacts at the active site, was essential for competitive inhibition of aldehyde reduction. This was due to selective binding to the AR:NADPH binary complex. In contrast, more aromatic inhibitors, which bind to the aldose reductase active site primarily via hydrophobic interactions, bind with greater affinity to the AR:NADP+ binary complex and thus behave as non-competitive inhibitors of aldehyde reduction, but competitive inhibitors of alcohol oxidation (19).

EXAMPLE 9

DCEG-based Inhibitor Design

Figure 4:
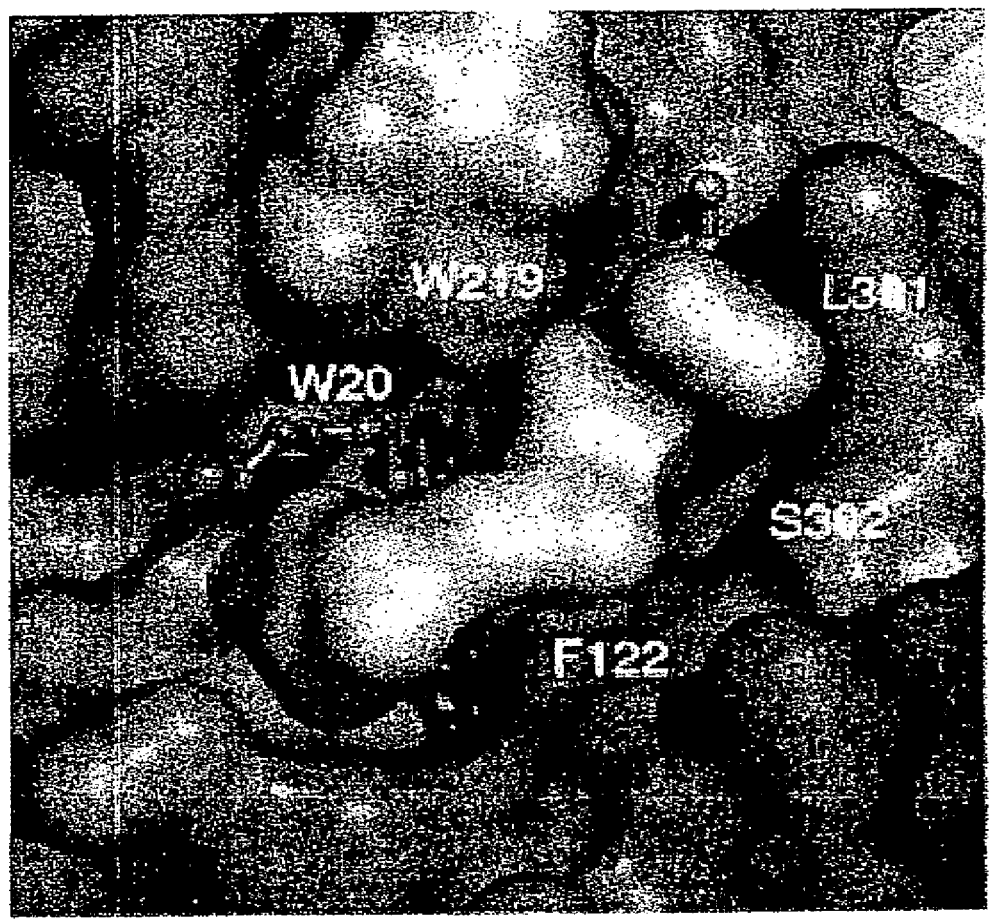
FIG. 4 is a model of a potential GS-like inhibitor with an aldehyde bound in the active site. An aldehyde chain (gold, green, or blue) may pass though one of three channels between the inhibitor (yellow) and protein (purple) to reach the AR active site. The mobile loops A, B, and C are colored as in FIGS. 2B and 3.

The structure of DCEG bound to aldose reductase provides a starting model for the design of an inhibitor of aldose reductase carbonyl metabolism which would not significantly interfere with aldose reductase detoxification of reactive aldehydes. The proposed GS-based inhibitor binding in the DCEG site would permit long alkyl chain peptides to reach the active site. Modeling of a DCEG-like selective inhibitor, based on the AR:NADPH:DCEG structure with an alkyl chain bound in the active site showed that there was more than one possible path for the alkyl chain to reach the active site (FIG. 4). Therefore, a DCEG-like inhibitor, lacking the active-site binding dicarboxyethyl moiety, could potentially block the binding of glucose and GS-conjugates while still permitting the entry and reduction of small to medium chain aliphatic aldehydes. By using such inhibitors, it might be possible to prevent the reduction of glucose to sorbitol in diabetics, conserve NADPH that can be used for the reduction of lipid peroxides and aldehydes, and regulate signaling pathways initiated by cytokines, chemokines, hyperglycemia, etc. without affecting the detoxification properties of AR that may be essential for reducing lipid aldehydes. Thus, a DCEG-based inhibitor might provide a therapeutic tool for regulating cytotoxic signals without inhibiting the detoxification role of aldose reductase.

EXAMPLE 10

Effect of AR Inhibition on Lipid Aldehyde-induced Signaling in Colon Cancer Cell Line (Caco-2)

AR is an excellent catalyst for the reduction of lipid peroxidation-derived aldehydes and their conjugates with glutathione to corresponding alcohols. The most abundant and toxic lipid aldehyde, 4-hydroxy-trans-2-nonenol (HNE) and its glutathione conjugate, GS-HNE are reduced by AR, in the presence of NADPH, to 1,4-dihydroxynonene (DHN) and GS-DHN, respectively with Km less than 30 mM (20, 21). HNE and its glutathione conjugate, GS-HNE, can be reduced by AR to 1,4-dihydroxynonene (DHN) and GS-DHN, respectively. Experiments were performed to see the effect of AR catalyzed reduction of lipid aldehydes is responsible for growth factor-induced expression of Cox-2 and production of PGE2.

Figure 5A:
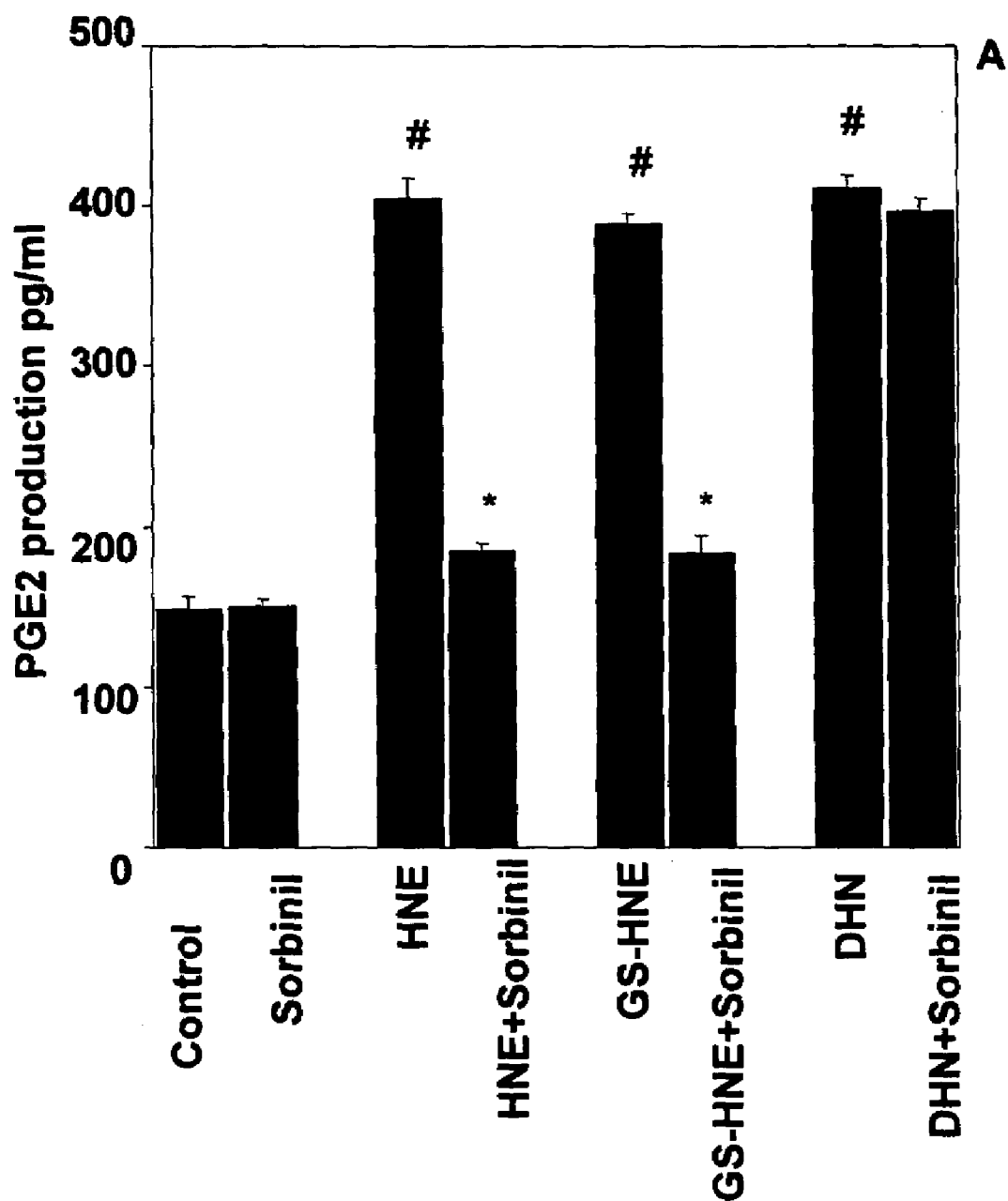
FIGS. 5A-5B illustrate the effect of AR catalyzed reaction products on production of PGE2 and expression of Cox-2 in Caco-2 cells. The Caco-2 cells were growth-arrested in 0.1% serum containing DMEM media without or with sorbinil (20 mM) for 24 h subsequently incubated with 0.75 mM each of HNE, GS-HNE-ester or GS-DHN-ester.
Figure 5B:
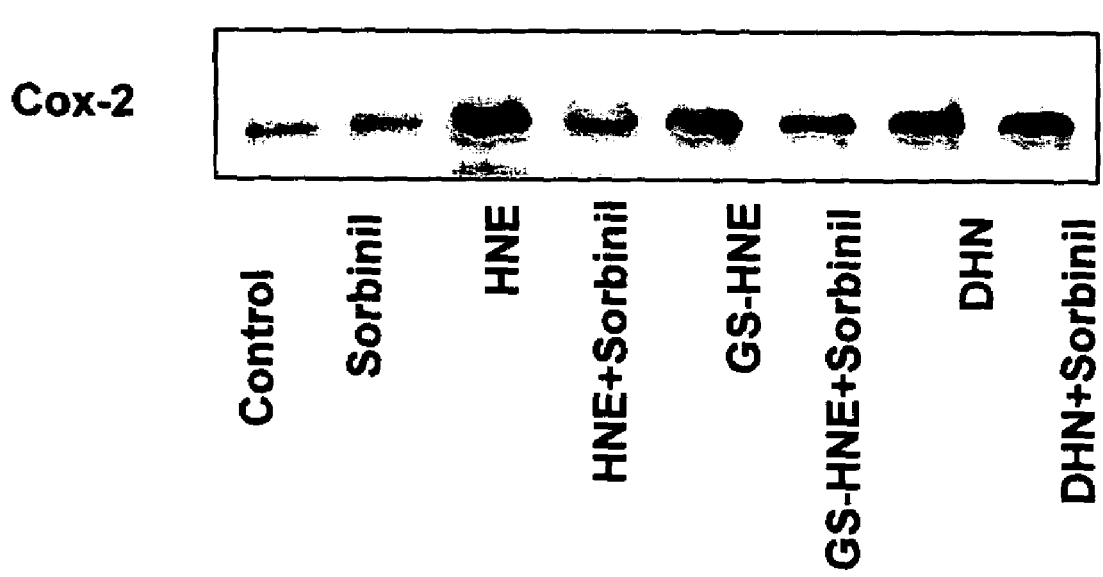

Growth-arrested Caco-2 cells incubated without or with sorbinil for 24 h were treated with 1 mM each of HNE, GS-HNE-ester or GS-DHN-ester for 24 h and the levels of PGE2 and Cox-2 were determined. Treatment of cells with HNE or ester of GS -HNE or GS-DHN resulted in increased PGE2 production (FIG. 5A) and also Cox-2 expression (FIG. 5B). Inhibition of AR by sorbinil significantly prevented the HNE or GS-HNE-induced Cox-2 expression and PGE2 production but had no effect on GS-DHN -induced expression of these inflammatory markers. These results indicate that growth factors-induced signaling might be mediated by GS-DHN and that the reduction of GS-HNE to GS-DHN by AR may be necessary for signaling cascade that up-regulates the expression of Cox-2 in colon cancer cells.

EXAMPLE 11

Effect of AR Inhibition on TNF-a Generation in High Glucose

Figure 6:
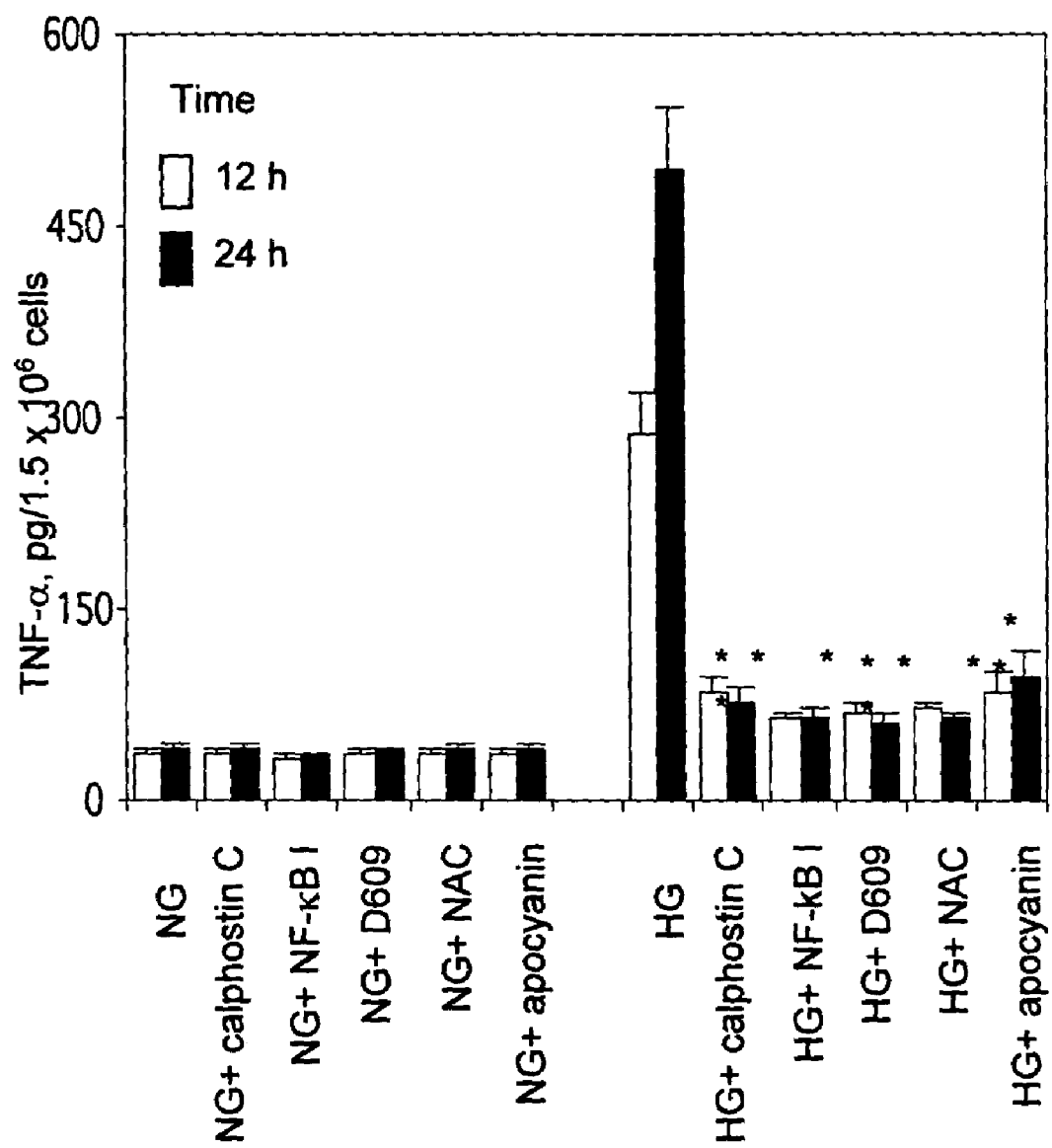
FIG. 6 illustrates the mechanism of high glucose-induced TNF-a production in rat VSMC. Growth-arrested VSMC in 5.5 mM glucose (NG) were preincubated for 1 h without or with apocyanin (25 mM), D609 (100 mM), calphostin C (0.2 mM), N-acetyl cysteine (10 mM) and NF-kB inhibitor (18 mM) respectively, followed by the addition of 19.5 mM glucose, after which the cells were incubated for indicated times. The data represent mean±SEM (n=4). **P<0.001 versus HG-treated cells.
Figure 7A:
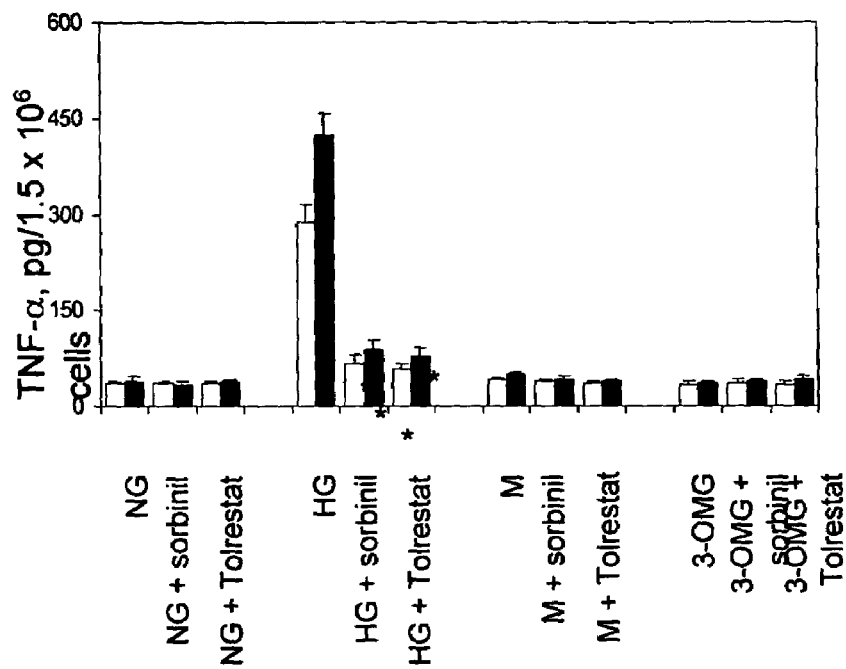
FIGS. 7A-7B illustrate the regulation of high glucose-induced TNF-a production by aldose reductase. Growth-arrested VSMC in 5.5 mM glucose (NG) were preincubated for 1 h without or with sorbinil or tolrestat (10 mM each) followed by the addition of glucose (19.5 mM) and incubation for the indicated times (FIG. 7A). AR antisense ablated VSMC were incubated with HG for the indicated times (FIG. 7B). The data represent mean±SEM (n=4). **P<0.001 versus cells incubated in high glucose.
Figure 7B:
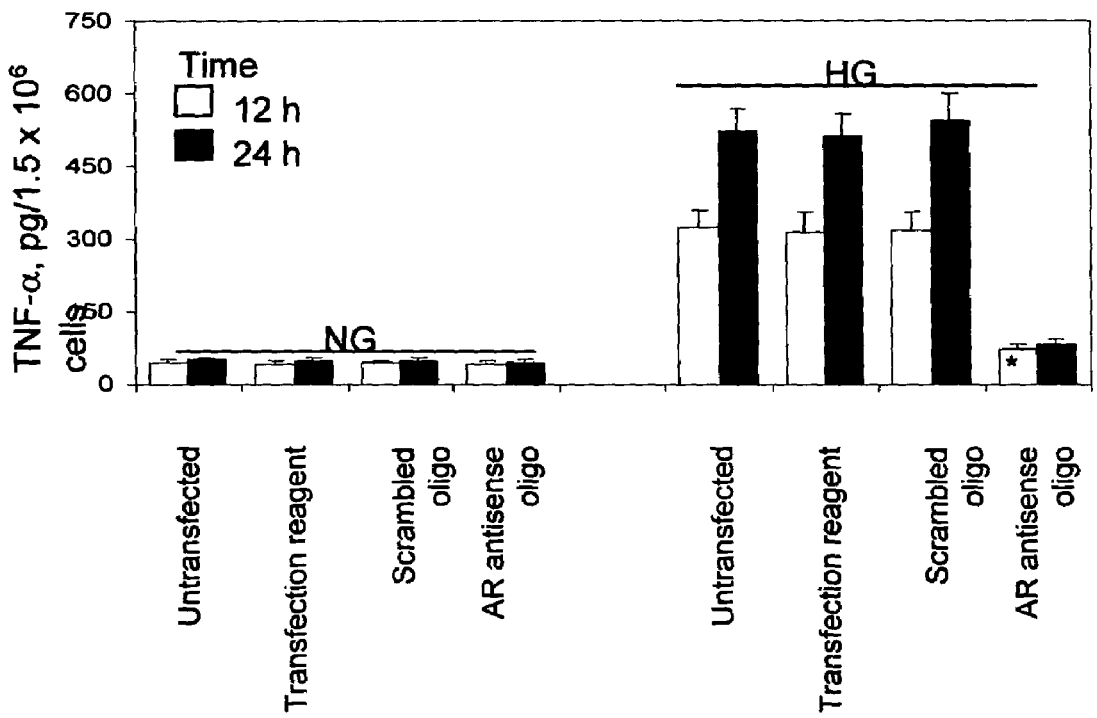

The effects of inhibiting PLC, NADPH oxidase and aldose reductase on the production of TNF-a in a culture medium (rat VSMC cells). As shown in FIG. 6, incubation with the PC-PLC inhibitor (calphostin C) markedly decreased TNF-a secretion. A similar decrease in TNF-a was observed in cells treated with the NADPH oxidase inhibitor apocyanin and the antioxidant N-acetylcysteine. Collectively, these observations support a mechanism in which high glucose increases TNF-a secretion by stimulating an intracellular signaling pathway that depends upon the activation of PLC and NADPH oxidase and the resultant change in the redox state of the cells. That this mechanism requires aldose reductase is suggested by data presented in FIGS. 7A and 7B, which show that either pharmacological inhibition of AR by treating cells with AR inhibitors sorbinil or tolrestat or antisense ablation of the AR gene prevents high glucose-induced TNF-a secretion. Treatment with AR inhibitors did not affect basal levels of TNF-a in media containing 5.5 mM glucose, mannitol, or 3-OMG. Moreover, high glucose-induced TNF-a production was not prevented in untransfected cells or cells incubated with the transfection medium or transfection medium containing scrambled oligonucleotides. These observations attest to the specificity of TNF-a generation on AR activity. Taken together, the signaling studies described above suggest that high glucose increases TNF-a secretion, by increasing aldose reductase and phospholipase C. These processes stimulate PKC and then NF-kB, which in turn increases transcription of the TNF-a gene.

EXAMPLE 12

Effect of AR Inhibition on NF-kB Mediated Inflammatory Response Induced by Bacterial Infection NF-kB is a central transcriptional regulator of inflammatory mediators. Reactive oxygen species (ROS) can stimulate nuclear localization and activation of NF-kB however the exact mechanism is unknown. A model of NF-kB activation induced by bacterial infection was used to study how ROS might activate NF-kB.

Figure 8A:
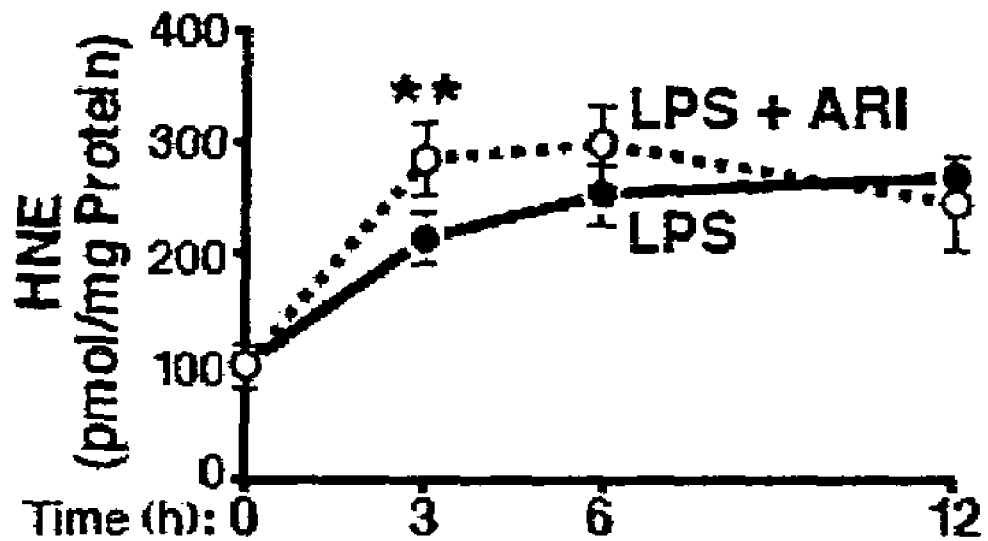
FIG. 8 illustrates the effect of AR inhibition/ablation on LPS- and lipid aldehyde-induced signaling in RAW264.7 cells. Cells were growth-arrested in Dulbecco's modified Eagle's medium (FIG. 8A-8D) containing 0.1% serum with or without sorbinil (10 mM) and challenged with LPS (1 mg/ml). At the indicated times, cells were harvested for measurement of HNE (FIG. 8A), protein-HNE adducts (FIG. 8B), NF-kB (FIG. 8C), and TNF-a and IL-6 (FIG. 8D) as described in the methods. Cells were growth arrested as described above or transfected with control or AR siRNA (FIGS. 8E-8F) oligonucleotides, incubated with GS-HNE-ester, or GS-DHN-ester (1 mM), and harvested for determination of NF-kB (FIG. 8E), membrane-bound total PKC (FIG. 8F).
Figure 8B:
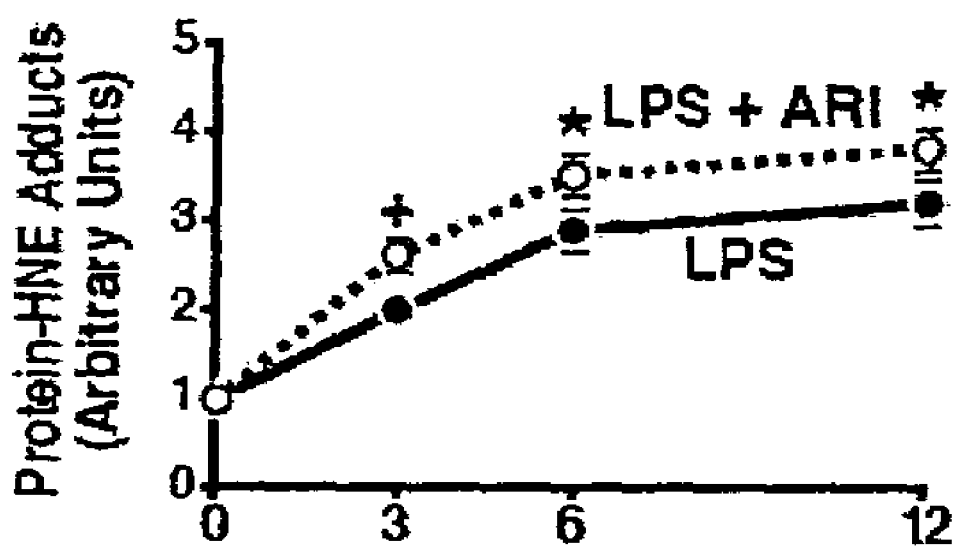
Figure 8C:
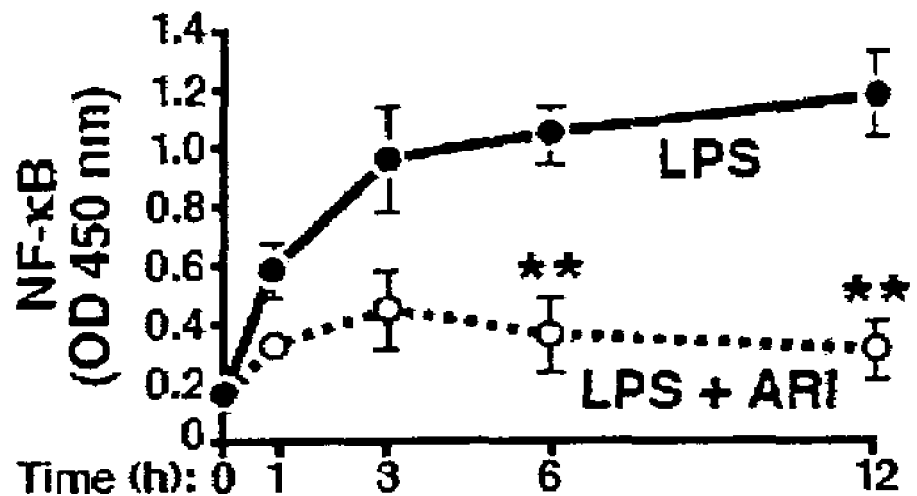
Figure 8D:
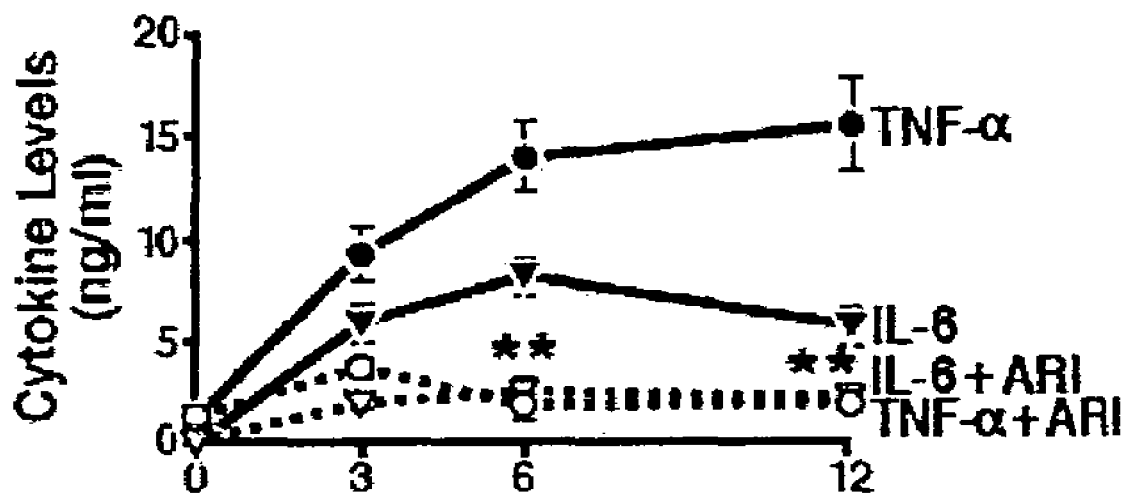
Figure 8E:
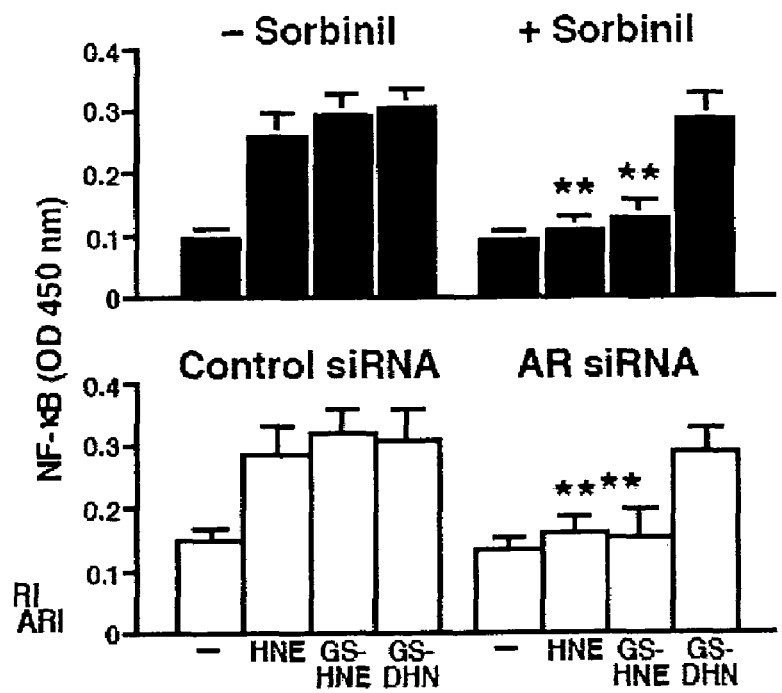

The effect of AR inhibition on 4-hydroxy-trans-2-nonenol (HNE) induction by bacterial lipopolysaccharide (LPS) was evaluated in RAW264.7 macrophages. LPS was found to increase HNE and protein-HNE adducts by nearly 3-fold within 6 h (FIGS. 8A and 8B). When AR was pharmacologically inhibited with sorbinil, HNE and protein-HNE adduct levels increased, consistent with a role for AR in reducing HNE. Inhibition of AR significantly decreased LPS-induced NF-kB and cytokine activation (FIGS. 8C and 8D). In macrophage cells, treatment with HNE/Glutathione (GS)-HNE or glutathione conjugate of 1,4-dihydroxynonene (GS-DHN) resulted in phosphorylation of IKK-ãb and translocation of NF-kB to the nucleus (FIG. 8E). Inhibition of AR with sorbinil or small interfering RNA (siRNA) targeting AR mRNA significantly blunted the effects of HNE/GS-HNE on IKK-ãb phosphorylation and NF-kB translocation but had no effect on the ability of GS-DHN, the already reduced form of GS-HNE, to activate NF-kB (FIG. 8E), suggesting that GS-DHN is sufficient for NF-kB translocation and is involved in IKK-ãb phosphorylation.

Figure 8F:
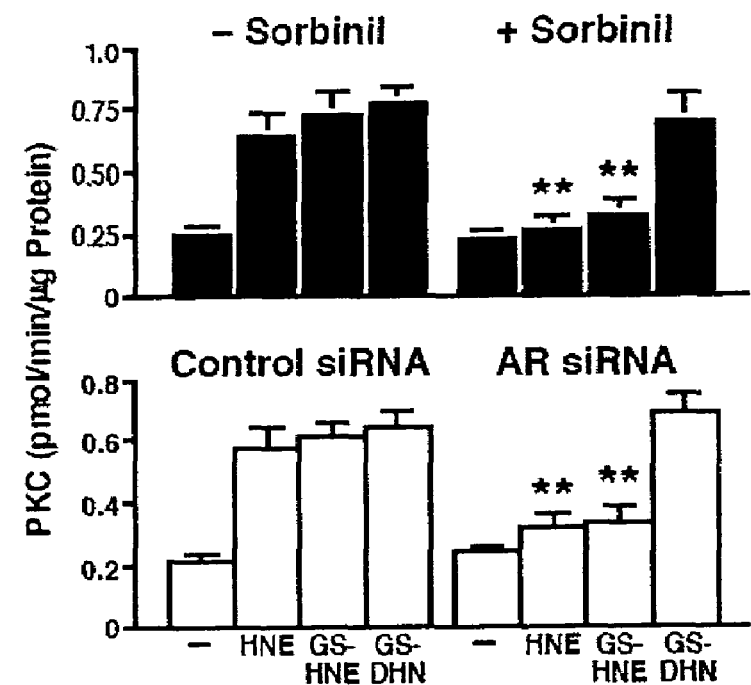

To determine if GS-DHN serves as a cellular sensor of ROS-induced insults, its effects on phosphorylation events upstream of IKK/NF-kB activation in RAW264.7 macrophages was examined. After GS-DHN challenge, the activity of protein kinase C (PKC), a kinase upstream of IKK increased by ~2.5 fold within 60 min (FIG. 8F). GS-DHN also induced phosphorylation of PLC-b3 and PLC-g1, which activate PKC but did not affect total PLC protein levels (not shown). HNE and GS-HNE had similar effects on the phosphorylation of the kinases upstream of NF-kB (FIG. 8F). However, pharmacologic inhibition of AR decreased the phosphorylation of PLC, PKC, and IKK induced by HNE and GS-HNE, but had no effect on GS-DHN-initiated phosphorylation of PLC and its downstream kinases (FIG. 8F). siRNA-mediated ablation of AR produced similar effects (FIG. 8F). These findings suggest that AR activity results in the production of reduced lipid aldehyde-glutathione conjugates that initiate an inflammatory cascade via PLC.

Figure 9A:
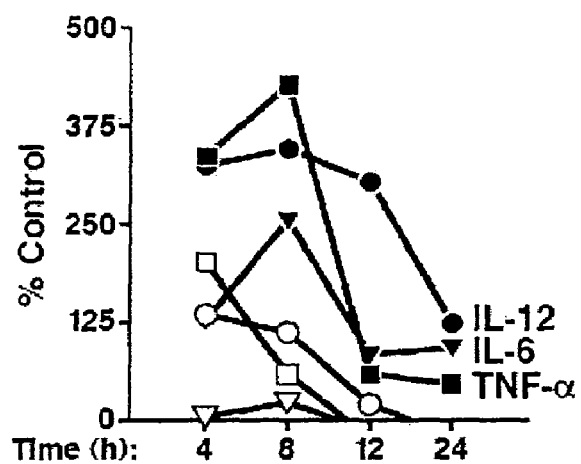
(FIGS. 9A-9D) At the indicated times, TNF-a, IL-6, IL-12, interferon (IFN)-g, IL-1b, and monocyte chemo attractant protein (MCP)-1 levels in serum and in heart homogenates were determined. Prostaglandin E2 (PGE-2), cyclooxygenase 2 (COX-2), and nitrate levels were measured Separately (FIG. 9E). Solid symbols, values from the mice injected with LPS; open symbols, values from the mice treated with LPS and sorbinil.
Figure 9B:
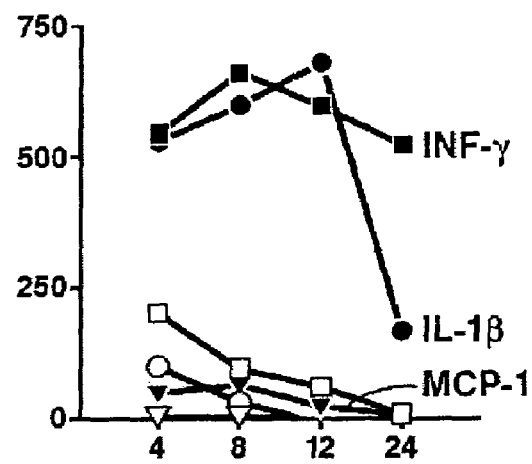
Figures 9C, 9D:
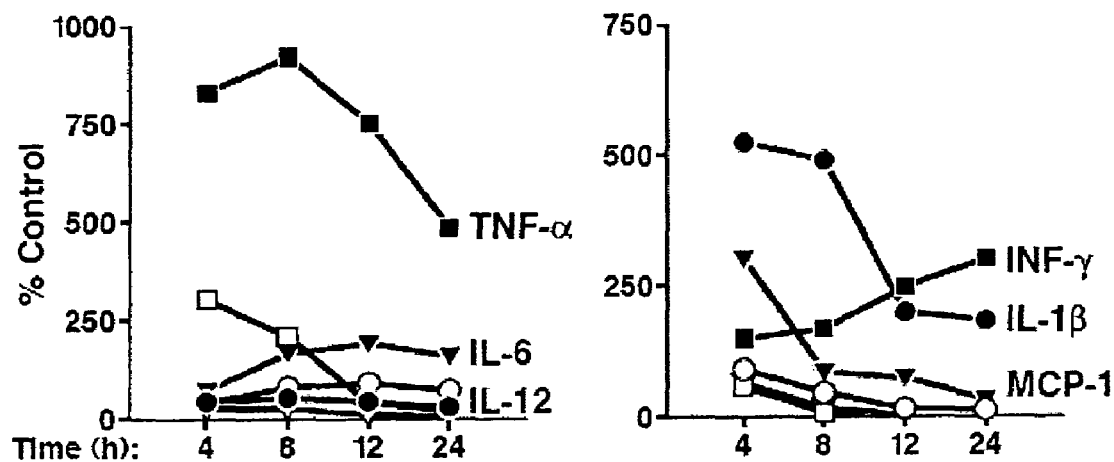
Figure 9E:
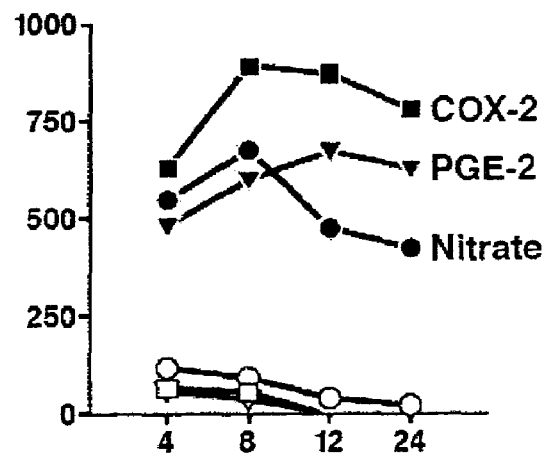
FIG. 9 illustrates the effect of AR inhibition on LPS-induced cytokines. C57BL/6 mice (N=6 per group) were injected with sorbinil or vehicle for 3 days, then challenged with LPS (4 mg/kg).

To investigate whether AR mediates the LPS signal in vivo, examined the effects of AR inhibition on NF-kB signaling pathways and myocardial dysfunction in a mouse model of overwhelming sepsis was examined. After pretreatment with sorbinil or vehicle alone, mice were injected peritoneally with a sub-lethal dose (4 mg/kg body wt) of LPS, and serum levels of inflammatory cytokines and chemokines were measured (FIGS. 9A and 9B). In controls, TNF-a, IL-6, IL-12, and interferon-g levels increased 3- to 6-fold within 8 h after LPS exposure and began declining by 24 h but remained elevated. In sorbinil-treated mice, however, serum cytokine levels increased only 2-fold, began declining within 4 h, and returned to baseline levels within 12 h. Remarkably, treatment with sorbinil 2 h after LPS exposure also blunted the maladaptive systemic inflammatory response in serum. Similar effects of AR inhibitor on cytokine and chemokine activation within the myocardium after LPS challenge was also observed (FIGS. 9A and 9C).

Figure 10A:
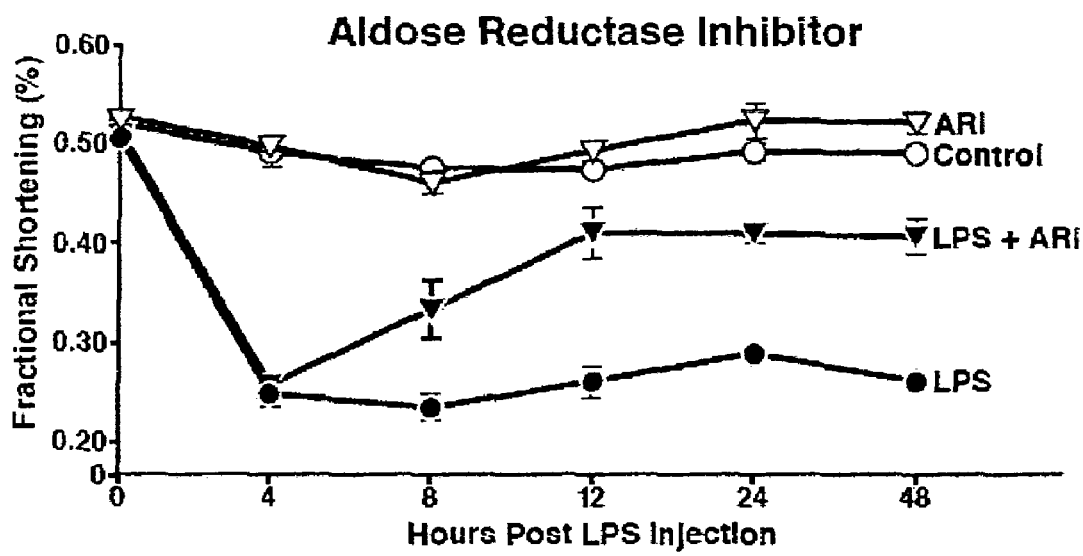
(FIG. 10A) C57BL/6 mice (N=6 per group) were treated as described in FIG. 9, and fractional shortening percent (FS %) was determined by M-mode echocardiography 0-48 h after LPS injection. Values are means of SD. The data were analyzed by one-way repeated-measures ANOVA.

To determine if AR inhibition could also rescue the cardiac dysfunction associated with the inflammatory response, serial echocardiography in LPS-challenged mice pretreated with sorbinil or vehicle and in unchallenged controls injected with vehicle or sorbinil was performed. In all LPS-challenged mice, percent fractional shortening (FS %) was depressed at 4 h after the injection; however, at 8 h, FS % had recovered significantly in the mice pretreated with sorbinil, but had deteriorated further in vehicle-injected controls (FIG. 10A). The functional recovery in the sorbinil group persisted at 12, 24, and 48 h, but FS % in the LPS challenged animals remained profoundly depressed. The FS % was not affected in unchallenged controls. Similar results were observed in mice given sorbinil 2 h after LPS challenge. The general activity level of LPS-exposed mice was consistent with the echocardiographic findings: sorbinil-treated mice exhibited normal grooming and other activities within 24 h, while LPS-treated mice remained inactive and huddled close to one another.

Figure 10B:
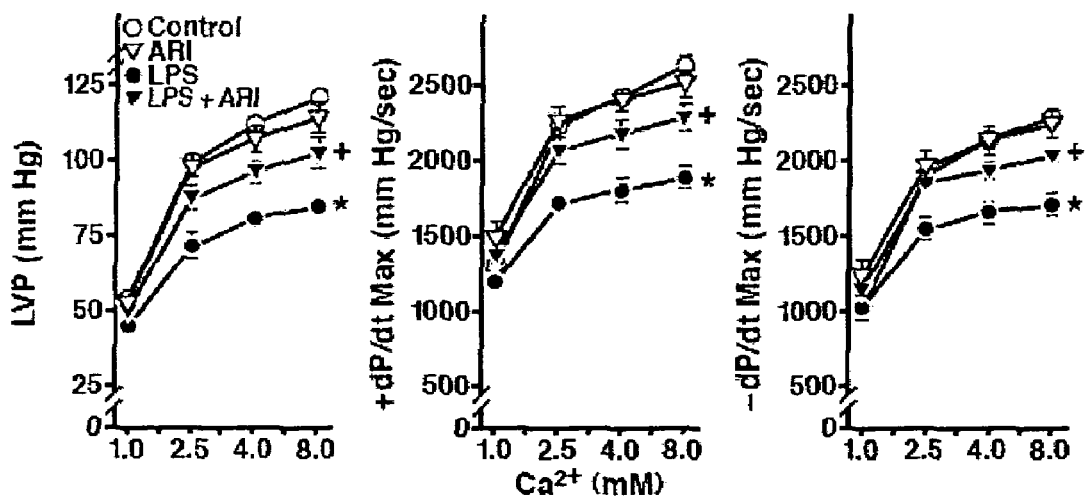
(FIGS. 10B and 10C) Cardiac function in isolated mouse hearts (Langendorff preparation) at various times after LPS challenge as a function of increasing $Ca^{2+}$ concentration (FIG. 10B) or coronary flow rate (FIG. 10C). Values are means±SEM of six independent experiments.
Figure 10C:
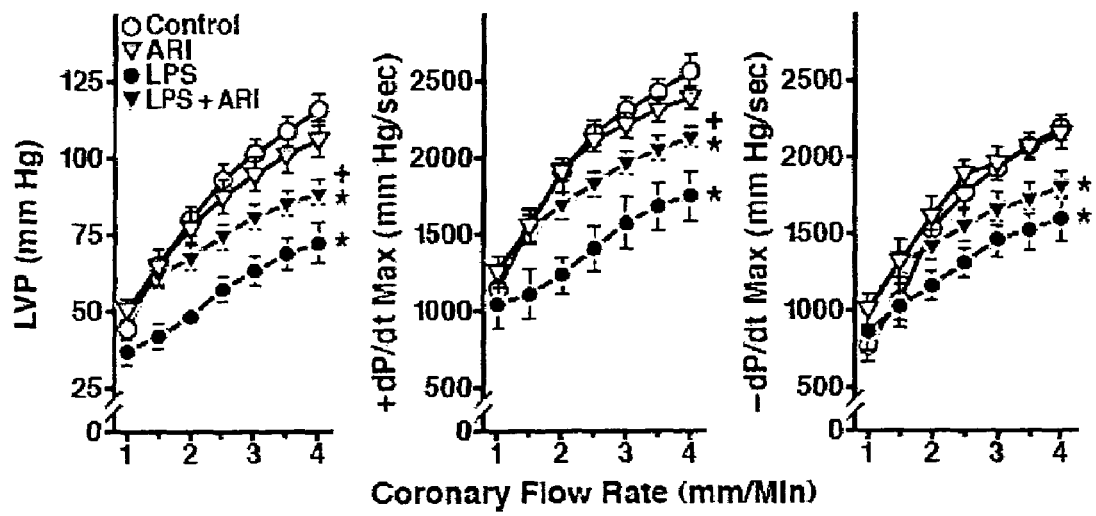

To more rigorously assess the effect of AR inhibition on cardiac function, spontaneously beating isolated mouse hearts (Langendorff preparation) were perfused with the AR inhibitor and challenged with LPS (FIGS. 10B and 10C). In the presence of LPS, perfusion with sorbinil significantly increased left ventricular pressure (LVP), the velocity of ventricular contraction (+dP/dtmax), and the velocity of ventricular relaxation (–dP/dtmax) compared to vehicle; the time to maximal ±dP/dt, coronary perfusion pressure, coronary vascular resistance, and heart rate were unaffected. When calcium concentration or coronary flow rate was increased, the differences in sorbinil-treated mice were further magnified (FIGS. 10B and 10C). These findings demonstrate that inhibition of AR activity rapidly improved the systolic and diastolic cardiac dysfunction induced by LPS.

Figure 10D:
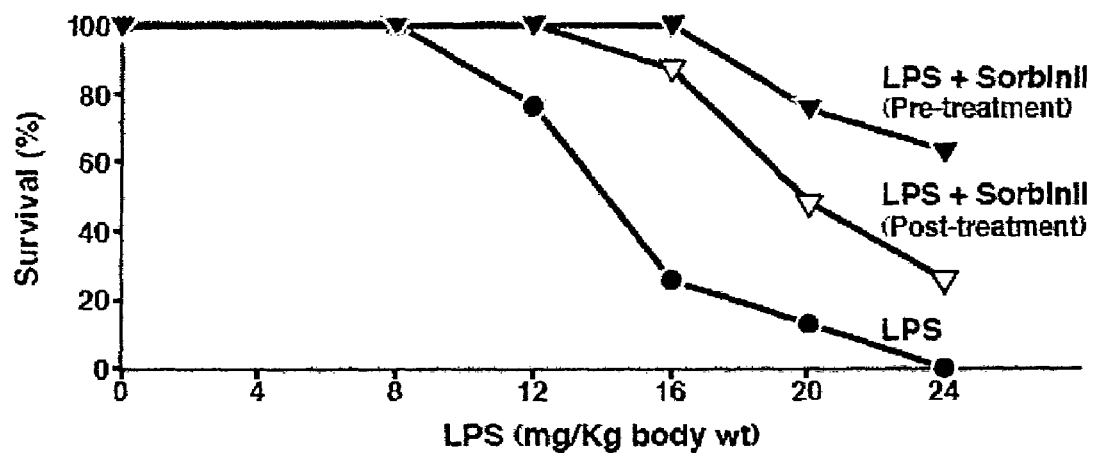
(FIG. 10D) Protective effect of AR inhibition on LPS-induced lethality. Percent (%) survival of mice 48 h after LPS administration at increasing doses or LPS plus sorbinil administration either 24 h before LPS (pre-treatment) or 2 h after LPS (post-treatment). The LD50 for LPS alone was 14 mg/kg, that with sorbinil pre-treatment was 24 mg/kg, and with sorbinil post-treatment was 20 mg/kg (N=8 per group, *p<0.001).

The above studies were performed with sublethal doses of LPS in order to assess effects on cardiac function. However, levels of LPS after bacterial sepsis often cause lethality in humans despite antibiotic therapy. Therefore increasing doses of LPS was administered to determine the dose at which fifty percent lethality occurred (LD50) in the presence or absence of aldose reductase inhibitor (ARI) in order to determine if ARI protected mice for LPS-induced death (FIG. 10D). It was found that the LD50 in control mice was 14 mg/kg LPS as previously reported. Remarkably, pre-treatment of mice with sorbinil resulted in approximately 90% survival at the same LPS dose and over 60% survival even with LPS doses as high as 24 mg/kg, which was a 100% lethal dose in controls by 48 hours. Administration of sorbinil two hours after LPS exposure, without pretreatment, still resulted in improved mortality compared to controls with an LD50 of 20 mg/kg (FIG. 10D). Thus, inhibition of AR prevented mortality associated with lethal doses of LPS.

Figure 11A:
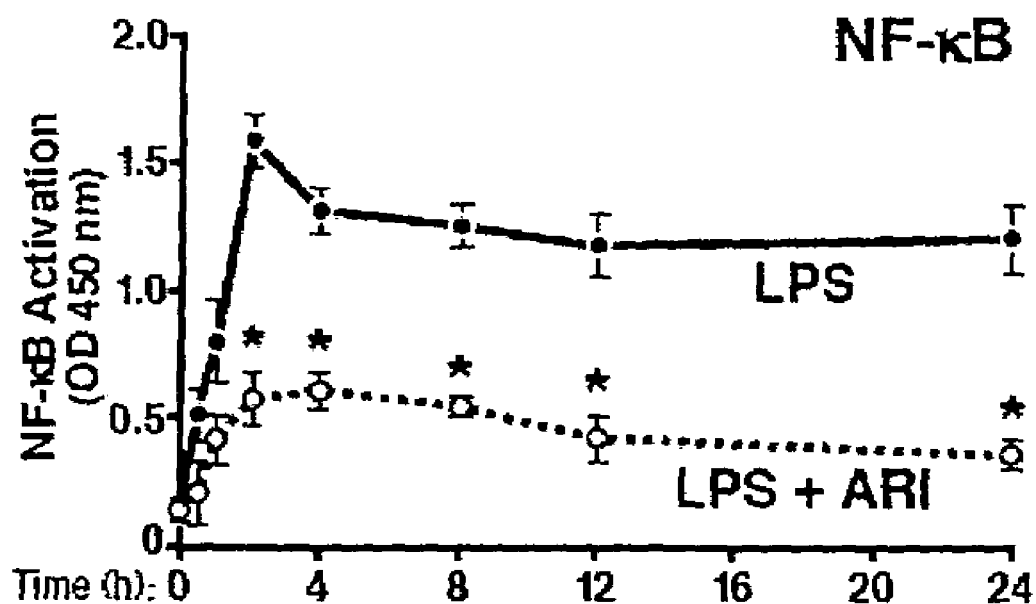
FIG. 11 illustrates the effect of AR inhibition on LPS signaling in the heart. C57BL/6 mice (N=6 per group) were treated as described in FIG. 9. At the indicated times, we measured (FIG. 11A) NF-kB activation, (FIG. 11B) AP1 activation with an electrophoretic mobility shift assay, (FIG. 11C) iNOS expression by western blotting, (FIG. 11D) PKC activation with a total PKC assay system (SignaTect, Promega), or (FIG. 11E) phosphorylated forms of the indicated kinases by western blotting. Values are means±SEM (N=4). *P<0.001 versus LPS-treated mice. OD, optical density.
Figure 11B:
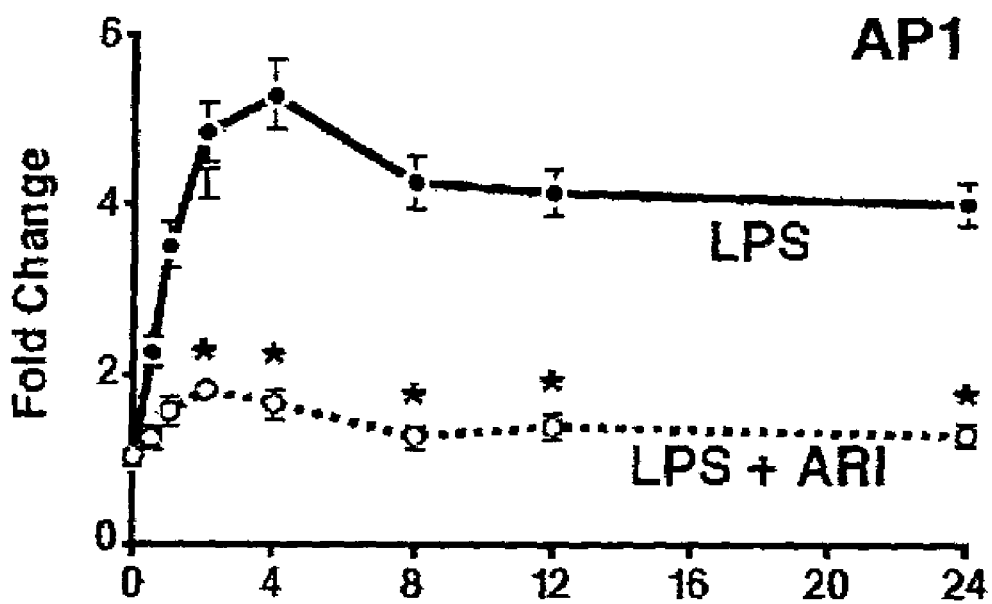
Figure 11C:
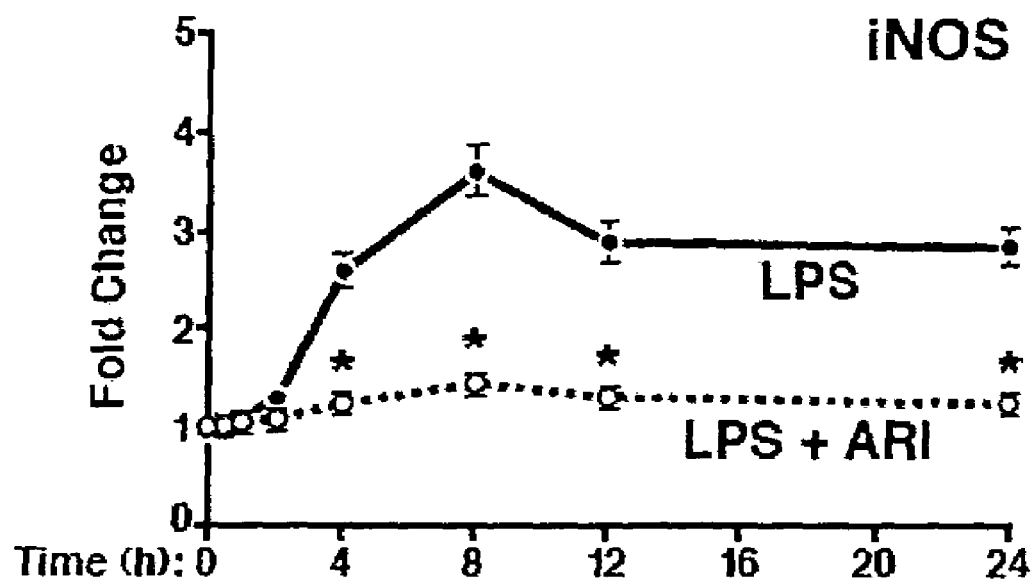
Figure 11D:
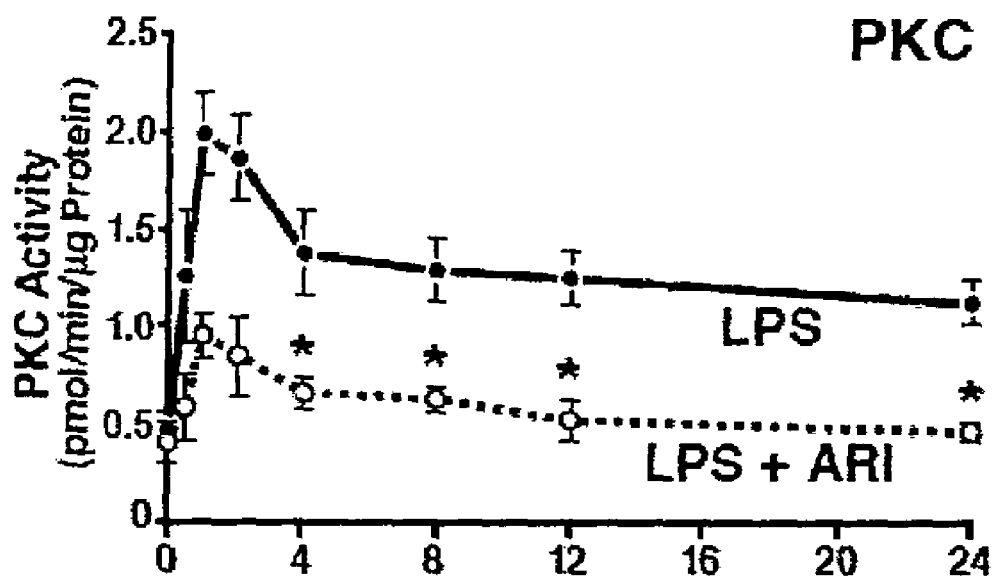
Figure 11E:
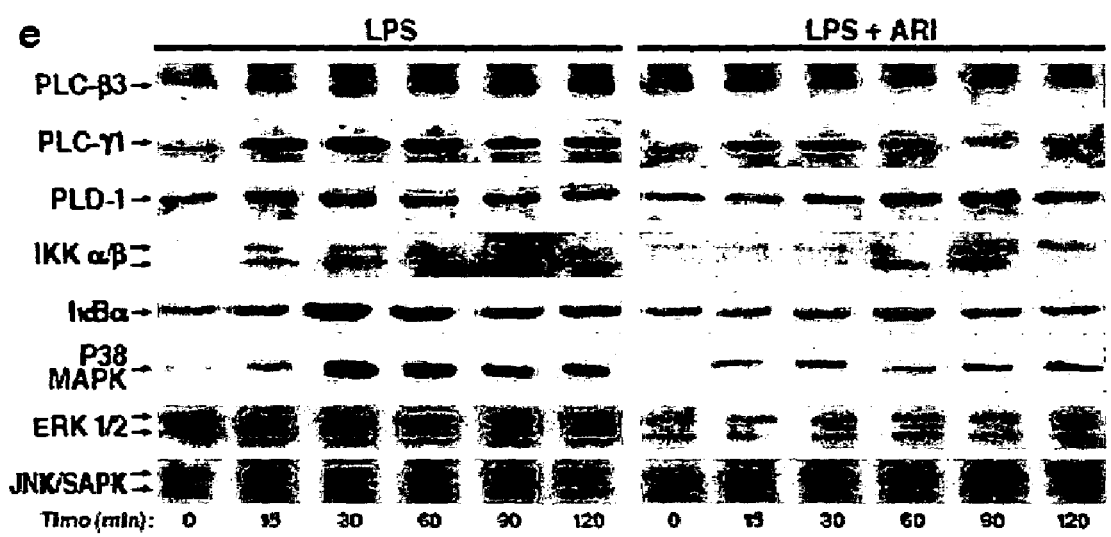

In untreated mice, LPS increased cardiac NF-kB activation by 16-fold and AP1 activation by 5-fold within 2 h, and the levels remained elevated even after 24 h (FIGS. 11A and 11B). In sorbinil-treated mice, however, activation of NF-kB and AP1 decreased by ~70% at 2 h, and the levels returned to baseline by 24 h. Similar results were observed in mice treated with sorbinil before or 2 h after LPS exposure. These findings are consistent with the downregulation of inflammatory cytokines and chemokines in the serum and heart upon AR inhibition (FIG. 11A-11E). Further, in response to LPS, cardiac iNOS levels increased by ~3-fold at 8 h and remained elevated at 24 h; however, in sorbinil-treated mice, iNOS levels increased only slightly and returned nearly to baseline levels by 24 h (FIG. 11C). As in macrophages, LPS significantly increased the phosphorylation of upstream kinases of NF-£eB and AP1 (e.g.,MAPK, IKK, PKC, and PLC) in the heart. AR inhibition attenuated the phosphorylation of almost all members of this cascade (FIGS. 11D and 11E). Thus, AR appears to inhibit the inflammatory cascade by regulating the activation of NF-kB, thereby protecting against cardiovascular collapse in the setting of overwhelming sepsis.

The following references were cited herein:
1. Jez, et al., (1997) *Biochem. J.* 326, 625-636.
2. Rondeau, et al., (1992) *Nature* 355, 469-72.

3. Wilson, et al., (1992) *Science* 257, 81-84.
4. Bhatnagar et al., (1992) *Biochem. Med. Metab. Biol.* 48, 91-121.
5. Nishikawa, et al., (2000) *Kidney Int. Suppl.* 77, S26-30.
6. Parry, G. J. (1999) *Am J Med* 107, 27S-33S.
7. Srivastava, et al., (1995) *Biochem. Biophys. Res. Commun.* 217, 741-746.
8. Srivastava, et al., (1998) *Biochem. J.* 329, 469-475.
9. Srivastava, et al., (1999) *Biochemistry* 38, 42-54.
10. van der Jagt, et al., (1992) *J. Biol. Chem.* 267, 4364-4369.
11. Kawamura, et al., (1999) *Biochem Pharmacol* 58, 517-24.
12. Rittner, et al., (1999) *J Clin Invest* 103, 1007-13.
13. Shinmura, et al., (2002) *Circ Res* 91, 240-6.
14. Ruef, et al., (2000) *Arterioscler Thromb Vasc Biol* 20, 1745-52.
15. Ramana, et al., (2002) *J Biol Chem* 277, 32063-70.
16. Uchida, K. (2003) *Prog Lipid Res* 42, 318-43.
17. Grimshaw, C. E. (1992) *Biochemistry* 31, 10139-45.
18. Varnai, P., Richards & Lyne (1999) *Proteins* 37, 218-27.
19. Dixit, et al., (2000) *J. Biol. Chem.* 275, 21587-21595.
20. Ramana, et al., (2000) *Biochemistry* 39, 12172-12180.
21. Ramana, et al., (2004) *FASEB J* 18, 1209-18.
22. Ramana, et al., (2004) *Diabetes* 53.
23. Petrash, et al., (1992) *J. Biol. Chem.* 267, 24833-24840.
24. Matthews, B. W. (1962) *J. Mol. Biol.* 33, 491-7.
25. Otwinowski, Z. & Minor, W. (1997) *Meth. Enz.* 276, 307-326.
26. Kissinger, et al., (2001) *Acta Crystallogr D Biol Crystallogr* 57, 1474-9.
27. Brunger et al., (1998) *Acta Crystallogr D Biol Crystallogr* 54 (Pt 5), 905-21.
28. Scott, et al., (2004) *J Biol Chem* 279, 27294-301.
29. Tickle, et al., (1998) *Acta Crystallogr D Biol Crystallogr* 54 (Pt 2), 243-52.
30. Tickle, et al., (1998) *Acta Crystallogr D Biol Crystallogr* 54 (Pt 4), 547-57.
31. Tickle, et al., (2000) *Acta Crystallogr D Biol Crystallogr* 56 (Pt 4), 442-50.
32. Brunger, A. T. (1992) *Nature* 355, 472-474.
33. McRee, D. E. (1999) *J Struct Biol* 125, 156-65.
34. Matthews, et al., (1975) *Acta Crystallogr* A31, 480-487.
35. Hynes, T. R. & Fox, R. O. (1991) *Proteins* 10, 92-105.
36. van Aalten et al., (1996) *J. of Computer Aided Molec Design* 10, 255-262.
37. Laskowski, et al., (1996) *J Biomol NMR.* 8, 477-86.
38. Murshudov, et al., (1999) *Acta Crystallogr D Biol Crystallogr* 55 (Pt 1), 247-255.
39. (1994) *Acta Cryst.* D 50, 760-763.
40. Delano, W. L. (2003) (Delano Scientific, San Carlos, Calif.).
41. Calderone et al., (2000) *Acta Crystallogr D Biol Crystallogr* 56, 536-40.
42. Urzhumtsev, et al., (1997) *Structure* 5, 601-12.
43. El-Kabbani, et al., (1998) *Mol Vis* 4, 19.
44. Bohren, et al., (1992) *J Biol Chem* 267, 20965-70.
45. Prade, et al., (1997) *Structure* 5, 1287-.
46. Sussman, et al., (1998) *Acta Crystallogr D Biol Crystallogr* 54, 1078-84.
47. Yang, et al., (1998) *Biochemistry* 37, 17145-56.
48. Bousset, et al., (2001) *Biochemistry* 40, 13564-.
49. Harrop, et al., (2001) *J. Biol. Chem.* 276, 44993-5000.
50. Becker, et al., (1998) *Nat Struct Biol* 5, 267-71.
51. Epp, et al., (1983) *Eur J Biochem* 133, 51-69.
52. Karplus, et al., (1989) *Eur J Biochem* 178, 693-703.
53. Kanaoka, et al., (1997) *Cell* 90, 1085-95.
54. Wilson, et al., (1993) *PNAS* 90, 9847-51.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. It will be apparent to those skilled in the art that various modifications and variations can be made in practicing the present invention without departing from the spirit or scope of the invention. Changes therein and other uses will occur to those skilled in the art which are encompassed within the spirit of the invention as defined by the scope of the claims.

What is claimed is:

1. A method of designing a potential inhibitor of glutathione-aldehyde conjugate binding to aldose reductase, comprising:
   (a) co-crystallizing the recombinant human aldose reductase of SEQ ID NO: 1 (AR) and nicotinamide dihydro nicotinamide adenine dinucleotide phosphate (NADPH) to provide an AR:NADPH co-crystal; and soaking the co-crystal with gamma-glutamyl-S-(1,2-dicarboxyethyl)cysteinylglycine (DCEG) to form a crystal of an AR:NADPH:DCEG ternary complex, wherein the crystal of the ternary complex has the space group of P21, unit cell dimensions of a=47.21 Å, b=66.72 Å, c=49.30 Å; and angles of α=90.00°, β=92.24°, γ=90.00°;
   (b) performing X-ray crystallography on the crystal of the ternary complex to determine a three-dimensional structure of the ternary complex;
   (c) generating a three-dimensional model of an active pocket of the AR; wherein the active pocket comprises a flexible A loop comprising residues Pro-123 to Val-131, a flexible B loop comprising residues Pro-218 to Pro-225, a flexible C loop comprising residues Ala-299 to Ser-302, a glutathione binding domain comprising residues Trp-20, Trp-79, Trp-111, Trp-219, Phe-122, Val-47, Cys-298, Ala-299, Ser-302, Leu-300, and Leu-301, and a carbonyl binding site comprising residues Tyr-48, His-110, and Trp-111, wherein the active pocket residues are according to SEQ ID NO: 1; and
   (d) identifying a potential inhibitor of glutathione-aldehyde conjugate binding to the aldose reductase active pocket using the three-dimensional model from step (c).

2. The method of claim 1, further comprising: (e) screening said potential inhibitor for inhibition of glutathione-aldehyde conjugate reduction by human aldose reductase.

3. The method of claim 2, wherein the screening step comprises: contacting the AR with said potential inhibitor and a glutathione-aldehyde conjugate and determining whether or not the potential inhibitor inhibits AR reduction of the glutathione-aldehyde conjugate.

4. The method of claim 1, wherein said potential inhibitor has a gamma-glutamylcysteinyiglycine backbone with an S-cysteinyl-substituted moiety.

5. A method of screening for a potential inhibitors of glutathione-aldehyde conjugate reduction by human aldose reductase, comprising:
- (a) co-crystallizing the recombinant human aldose reductase of SEQ ID NO: 1 (AR) and nicotinamide dihydro nicotinamide adenine dinucleotide phosphate (NADPH) to provide an AR:NADPH co-crystal and soaking the co-crystal with gamma-glutamyl-S-(1,2-dicarboxyethyl)cysteinylglycine (DCEG) to form a crystal of an AR:NADPH:DCEG ternary complex, wherein the crystal of the ternary complex has the space group of P21, unit cell dimensions of a=47.21 Å, b=66.72 Å, c=49.30 Å; and angles of $\alpha$=90.00°, $\beta$=92.24°, $\gamma$=90.00°;
- (b) performing X-ray crystallography on the crystal of the ternary complex to determine a three-dimensional structure of the ternary complex;
- (c) generating a three-dimensional model of an active pocket of the AR; wherein the active pocket comprises a flexible A loop comprising residues Pro-123 to Val-131, a flexible B loop comprising residues Pro-218 to Pro-225, a flexible C loop comprising residues Ala-299 to Ser-302, a glutathione binding domain comprising residues Trp-20, Trp-79, Trp-111, Trp-219, Phe-122, Val-47, Cys-298, Ala-299, Ser-302, Leu-300, and Leu-301, and a carbonyl binding site comprising residues Tyr-48, His-110, and Trp-111, wherein the active pocket residues are according to SEQ ID NO: 1;
- (d) identifying a potential inhibitor of glutathione-aldehyde conjugate reduction by aldose reductase using the three dimensional model of the aldose reductase active pocket from step (c);
- (e) contacting the AR with said potential inhibitor and a glutathione-aldehyde conjugate; and
- (f) determining whether or not the potential inhibitor inhibits AR reduction of the glutathione-aldehyde conjugate.

* * * * *

SEQUENCE LISTING

```
<160> NUMBER OF SEQ ID NOS: 1

<210> SEQ ID NO 1
<211> LENGTH: 315
<212> TYPE: PRT
<213> ORGANISM: artificial sequence
<220> FEATURE:
<223> OTHER INFORMATION: sequence of recombinant human aldose reductase

<400> SEQUENCE: 1

Ala Ser Arg Leu Leu Leu Asn Asn Gly Ala Lys Met Pro Ile Leu
1               5                   10                  15

Gly Leu Gly Thr Trp Lys Ser Pro Pro Gly Gln Val Thr Glu Ala
                20                  25                  30

Val Lys Val Ala Ile Asp Val Gly Tyr Arg His Ile Asp Cys Ala
                35                  40                  45

His Val Tyr Gln Asn Glu Asn Glu Val Gly Val Ala Ile Gln Glu
                50                  55                  60

Lys Leu Arg Glu Gln Val Val Lys Arg Glu Glu Leu Phe Ile Val
```

-continued

|  |  |  |  |  |  |  |  |  |  |  |  |
|---|---|---|---|---|---|---|---|---|---|---|---|
|  |  |  |  | 65 |  |  |  | 70 |  |  | 75 |
| Ser | Lys | Leu | Trp | Cys | Thr | Tyr | His | Glu | Lys | Gly | Leu | Val | Lys | Gly |
|  |  |  |  | 80 |  |  |  | 85 |  |  | 90 |
| Ala | Cys | Gln | Lys | Thr | Leu | Ser | Asp | Leu | Lys | Leu | Asp | Tyr | Leu | Asp |
|  |  |  |  | 95 |  |  |  | 100 |  |  | 105 |
| Leu | Tyr | Leu | Ile | His | Trp | Pro | Thr | Gly | Phe | Lys | Pro | Gly | Lys | Glu |
|  |  |  |  | 110 |  |  |  | 115 |  |  | 120 |
| Phe | Phe | Pro | Leu | Asp | Glu | Ser | Gly | Asn | Val | Val | Pro | Ser | Asp | Thr |
|  |  |  |  | 125 |  |  |  | 130 |  |  | 135 |
| Asn | Ile | Leu | Asp | Thr | Trp | Ala | Ala | Met | Glu | Glu | Leu | Val | Asp | Glu |
|  |  |  |  | 140 |  |  |  | 145 |  |  | 150 |
| Gly | Leu | Val | Lys | Ala | Ile | Gly | Ile | Ser | Asn | Phe | Asn | His | Leu | Gln |
|  |  |  |  | 155 |  |  |  | 160 |  |  | 165 |
| Val | Glu | Met | Ile | Leu | Asn | Lys | Pro | Gly | Leu | Lys | Tyr | Lys | Pro | Ala |
|  |  |  |  | 170 |  |  |  | 175 |  |  | 180 |
| Val | Asn | Gln | Ile | Glu | Cys | His | Pro | Tyr | Leu | Thr | Gln | Glu | Lys | Leu |
|  |  |  |  | 185 |  |  |  | 190 |  |  | 195 |
| Ile | Gln | Tyr | Cys | Gln | Ser | Lys | Gly | Ile | Val | Val | Thr | Ala | Tyr | Ser |
|  |  |  |  | 200 |  |  |  | 205 |  |  | 210 |
| Pro | Leu | Gly | Ser | Pro | Asp | Arg | Pro | Trp | Ala | Lys | Pro | Glu | Asp | Pro |
|  |  |  |  | 215 |  |  |  | 220 |  |  | 225 |
| Ser | Leu | Leu | Glu | Asp | Pro | Arg | Ile | Lys | Ala | Ile | Ala | Ala | Lys | His |
|  |  |  |  | 230 |  |  |  | 235 |  |  | 240 |
| Asn | Lys | Thr | Thr | Ala | Gln | Val | Leu | Ile | Arg | Phe | Pro | Met | Gln | Arg |
|  |  |  |  | 245 |  |  |  | 250 |  |  | 255 |
| Asn | Leu | Val | Val | Ile | Pro | Lys | Ser | Val | Thr | Pro | Glu | Arg | Ile | Ala |
|  |  |  |  | 260 |  |  |  | 265 |  |  | 270 |
| Glu | Asn | Phe | Lys | Val | Phe | Asp | Phe | Glu | Leu | Ser | Ser | Gln | Asp | Met |
|  |  |  |  | 275 |  |  |  | 280 |  |  | 285 |
| Thr | Thr | Leu | Leu | Ser | Tyr | Asn | Arg | Asn | Trp | Arg | Val | Cys | Ala | Leu |
|  |  |  |  | 290 |  |  |  | 295 |  |  | 300 |
| Leu | Ser | Cys | Thr | Ser | His | Lys | Asp | Tyr | Pro | Phe | His | Glu | Glu | Phe |
|  |  |  |  | 305 |  |  |  | 310 |  |  | 315 |